US005856302A

United States Patent [19]
Ammons et al.

[11] Patent Number: 5,856,302
[45] Date of Patent: *Jan. 5, 1999

[54] THERAPEUTIC USES OF BACTERICIDAL/ PERMEABILITY-INCREASING PROTEIN DIMER PRODUCTS

[75] Inventors: William Steve Ammons, Pinole; Roger G. Little, Benicia, both of Calif.

[73] Assignee: XOMA Corporation, Berkeley, Calif.

[ * ] Notice: The term of this patent shall not extend beyond the expiration date of Pat. Nos. 5,447,913 and 5,703,038.

[21] Appl. No.: 704,504

[22] PCT Filed: Mar. 13, 1995

[86] PCT No.: PCT/US95/03125

§ 371 Date: Dec. 16, 1996

§ 102(e) Date: Dec. 16, 1996

[87] PCT Pub. No.: WO95/24209

PCT Pub. Date: Sep. 14, 1995

Related U.S. Application Data

[63] Continuation-in-part of Ser. No. 212,132, filed as PCT/US95/03125 Mar. 13, 1995, Pat. No. 5,447,913.

[51] Int. Cl.⁶ .......... C07K 14/435; A61K 38/17
[52] U.S. Cl. .......... 514/12; 514/2; 424/192.1; 530/350
[58] Field of Search .......... 514/2, 12; 530/350; 435/69.1, 69.7; 424/192.1

[56] References Cited

U.S. PATENT DOCUMENTS

| | | | |
|---|---|---|---|
| 5,089,274 | 2/1992 | Marra et al. | 424/534 |
| 5,198,541 | 3/1993 | Elsbach et al. | 435/69.1 |
| 5,225,538 | 7/1993 | Capon et al. | 530/387.3 |
| 5,348,942 | 9/1994 | Little II et al. | 514/12 |
| 5,420,019 | 5/1995 | Theofan et al. | 435/69.1 |
| 5,439,807 | 8/1995 | Grinna | 435/69.1 |
| 5,447,913 | 9/1995 | Ammons et al. | 514/12 |
| 5,494,896 | 2/1996 | Hansbrough | 514/12 |
| 5,523,288 | 6/1996 | Cohen et al. | 514/12 |
| 5,578,568 | 11/1996 | Ammons et al. | 514/12 |
| 5,627,153 | 5/1997 | Little, II et al. | 514/12 |
| 5,639,727 | 6/1997 | Little, II | 514/12 |
| 5,641,874 | 6/1997 | Elsbach et al. | 536/23.1 |
| 5,643,570 | 7/1997 | Theofan et al. | 424/134.1 |
| 5,643,875 | 7/1997 | Friedmann et al. | 514/12 |

FOREIGN PATENT DOCUMENTS

| | | | |
|---|---|---|---|
| 93/23434 | 11/1993 | WIPO | C07K 15/00 |
| 93/23540 | 11/1993 | WIPO | C12N 15/12 |
| 94/17819 | 8/1994 | WIPO | A61K 37/02 |
| 94/18323 | 8/1994 | WIPO | C12N 15/12 |
| 94/20128 | 9/1994 | WIPO | A61K 37/02 |
| 94/20129 | 9/1994 | WIPO | A61K 37/02 |
| 94/20532 | 9/1994 | WIPO | C07K 7/06 |
| 95/02414 | 1/1995 | WIPO | A61K 38/17 |
| 95/08344 | 3/1995 | WIPO | A61K 38/17 |
| 95/10297 | 4/1995 | WIPO | A61K 38/17 |
| 95/19179 | 7/1995 | WIPO | A61K 38/17 |
| 95/19180 | 7/1995 | WIPO | A61K 38/17 |
| 95/19372 | 7/1995 | WIPO | C07K 14/47 |
| 95/19784 | 7/1995 | WIPO | A61K 38/17 |
| 96/21436 | 7/1996 | WIPO | A61K 31/17 |

OTHER PUBLICATIONS

Elsbach et al., "Separation and Purification of a Potent Bactericidal/Permeability—increasing Protein and a Closely Associated Phospholipase $A_2$ from Rabbit Polymorphonuclear Leukocytes," *J. Biol. Chem.*, 254(21):11000–11009 (1979) (not enclosed).

Elsbach et al., "Oxygen–Independent Antimicrobial Systems of Phagocytes" *Inflammation: Basic Principles and Clinical Correlates, Second Edition,* edited by Gallin et al., Chapter 30, Raven Press, Ltd. 603–636 (1992) (not enclosed).

Engleka et al., "Inactivation of Human Fibroblast Growth Factor–1 (FGF–1) Activity by Interaction with Copper Ions Involves FGF–1 Dimer Formation Induced by Copper–catalyzed Oxidation," *J. Biol. Chem.*, 267(16):11307–11315 (1992) (not enclosed).

Folkman et al., "Angiogenesis and Inflammation", *Inflammation: Basic Principles and Clinical Correlates, Second Edition,* Chapter 40, 821–839 (1992) (not enclosed).

Gazzano–Santoro et al., "High–Affinity Binding of the Bactericidal/Permeability–Increasing Protein and a Recombinant Amino–Terminal Fragment to the Lipid A Region of Lipopolysaccharide," *Infect. Immun.,* 60(1):4754–4761 (1992) (not enclosed).

Gray et al., "Cloning of the cDNA of a Human Neutrophil Bactericidal Protein," *J. Biol. Chem.*, 264(16):9505–9509 (1989) (not enclosed).

Hartmann et al., "Two dominant–acting selectable markers for gene transfer studies in mammalian cells" *Proc. Natl. Acad. Sci. (USA),* 85:8047–8051 (1988) (not enclosed).

In't Veld et al., "Effects of the Bactericidal/Permeability–Increasing Protein of Polymorphonuclear Leukocytes on Isolated Bacterial Cytoplasmic Membrane Vesicles," *Infect. Immun.,* 56(5):1203–1208 (1988) (not enclosed).

Kozak, "An analysis of 5'–noncoding sequences from 699 vertebrate messenger RNAs," *Nucl. Acid. Res.,* 15(20):8125–8148 (1987) (not enclosed).

Liu et al., "Production of a Mouse–Human Chimeric Monoclonal Antibody to CD20 With Potent Fc–Dependent Biologic Activity", *J. Immunol.,* 139(10):3521–3526 (1987) (not enclosed).

Mannion et al., "Separation of Sublethal and Lethal Effects of Polymorphonuclear Leukocytes on *Escherichia coli,*" *J. Clin. Invest.,* 86:631–641 (1990) (not enclosed).

(List continued on next page.)

*Primary Examiner*—Lorraine Spector
*Attorney, Agent, or Firm*—Marshall, O'Toole, Gerstein, Murray & Borun

[57] ABSTRACT

Improved therapeutic compositions, methods and uses of bactericidal/permeability-increasing protein (BPI) products involve use of dimeric forms of BPI protein product monomers characterized by enhanced in vivo biological activity. Preferred formulations include 50 percent or more by weight dimeric product and preferred therapeutic uses include endotoxin neutralization and heparin neutralization.

16 Claims, 12 Drawing Sheets

OTHER PUBLICATIONS

Morrison et al., "Endotoxins And Disease Mechanisms" *Ann. Rev. Med.,* 38:417–432 (1987) (not enclosed).

Morrison, "The case for specific lipopolysaccharide receptors expressed on mammalian cells," *Microb. Path.,* 7:389–398 (1989) (not enclosed).

Mulligan et al., Selection for animal cells that express the *Escherichia coli* gene coding for xanthine–guanine phosphoribosyltransferase, *Proc. Natl. Acad. Sci. (USA),* 78(4):2072–2076 (1981) (not enclosed).

Ooi et al., "Endotoxin–neutralizing Properties of the 25 kD N–Terminal Fragment and a Newly Isolated 30 kD C–Terminal Fragment of the 55–60 kD Bactericidal/Permeability–increasing Protein of Human Neutrophils," *J. Exp. Med.,* 174:649–655 (1991) (not enclosed).

Passaniti et al., "Method in Laboratory Investigation, A Simple, Quantitative Method for Assessing Angiogenesis and Antiangiogenic Agents Using Reconstituted Basement Membrane, Heparin, an Fibroblast Growth Factor," *Lab. Invest.,* 67(4):519–528 (1992) (not enclosed).

Raetz, "Biochemistry of Endotoxins," *Ann. Rev. Biochem.,* 59:129–170 (1990) (not enclosed).

Roeder et al., "Endotoxic–Lipopolysaccharide–Specific Binding Proteins on Lymphoid Cells of Various Animal Species: Association with Endotoxin Susceptibility," *Infect. Immun.,* 57(4):1054–1058 (1989) (not enclosed).

Sambrook et al., "Introduction of Recombinant Vectors into Mammalian Cells" *Molecular Cloning, A Laboratory Manual,* Cold Spring Laboratory Harbor Press, 16.30–16.31 (1989) (not enclosed).

Southern et al., "Transformation of Mammalian Cells to Antibiotic Resistance with a Bacterial Gene Under Control of the SV40 Early Region Promoter", *J. Mol. Appl. Genet.,* 1:327–341 (1982) (not enclosed).

Weiss et al., "Resistance of Gram–negative Bacteria to Purified Bactericidal Leukocyte Proteins," *J. Clin. Invest.* 65:619–628 (1980) (not enclosed).

Weiss et al., "The Role of Lipopolysaccharides In The Action Of The Bactericidal/Permeability–Increasing Neutrophil Protein on the Bacterial Envelope", *J. Immunol.,* 132(6):3109–3115 (1984) (not enclosed).

Weiss et al., "Cellular and Subcellular Localization of the Bactericidal/Permeability–Increasing Protein of Neutrophils," *Blood,* 69(2):652–659.

Xu et al., "Transcription Termination and Chromatin Structure of the Active Immunoglobulin K Gene Locus", *J. Biol. Chem.* 261(8):3838–3845 (1986) (not enclosed).

Yayon et al., "Cell Surface, Heparin–like Molecules Are Required for Binding of Basic Fibroblast Growth Factor to Its High Affinity Receptor", *Cell,* 64:841–848 (1991) (not enclosed).

THERAPEUTIC USES OF BACTERICIDAL/PERMEABILITY-INCREASING PROTEIN DIMER PRODUCTS

This is a national stage of International Application No. PCT/US95/03125, and is a continuation-in-part of U.S. application Ser. No. 08/212,132 filed Mar. 11, 1994, which issued as U.S. Pat. No. 5,447,913.

BACKGROUND OF THE INVENTION

The present invention provides bactericidal/permeability-increasing protein (BPI) dimer products characterized by enhanced in vivo biological activity and stable pharmaceutical compositions containing the same.

Lipopolysaccharide (LPS) is a major component of the outer membrane of gram-negative bacteria and consists of serotype-specific O-side-chain polysaccharides linked to a conserved region of core oligosaccharide and lipid A. Raetz, *Ann. Rev. Biochem.*, 59:129–170 (1990). LPS is an important mediator in the pathogenesis of gram-negative septic shock, one of the major causes of death in intensive-care units in the United States. Morrison, et al., *Ann. Rev. Med.* 38:417–432 (1987).

LPS-binding proteins have been identified in various mammalian tissues. Morrison, *Microb. Pathol.*, 7:389–398 (1989); Roeder, et al., *Infect., Immun.*, 57: 1054–1058 (1989). Among the most extensively studied of the LPS-binding proteins is bactericidal/permeability-increasing protein (BPI), a basic protein found in the azurophllic granules of polymorphonuclear leukocytes. Human BPI protein has been isolated from polymorphonuclear neutrophils by acid extraction combined with either ion exchange chromatography [Elsbach, *J. Biol. Chem.*, 254:11000 (1979)] or *E. coli* affinity chromatography [Weiss, et al., *Blood,* 69:652 (1987)] and has potent bactericidal activity against a broad spectrum of gram-negative bacteria.

The amino acid sequence of the entire human BPI protein, as well as the DNA encoding the protein, have been elucidated in FIG. 1 of Gray, et al., *J. Biol. Chem.*, 264:9505 (1989), incorporated herein by reference (SEQ ID NOS: 1 and 2). The Gray et al. publication discloses the isolation of human BPI-encoding cDNA from a cDNA library derived from DMSO-induced cells of the human promyelocytic leukemia HL-60 cell line (ATTC CCL 240). Multiple PCR amplifications of DNA from cDNA library derived from such DMSO-induced HL-60 cells as well as DNA from normal human blood and bone marrow cell have revealed the existence of human BPI-encoding cDNAs wherein the codon specifying valine at amino acid position 151 is either GTC (as set out in SEQ ID No: 1) or GTG. Moreover, cDNA species employing GTG to specify valine at position 151 have also been found to specify either lysine (AAG) for the position 185 amino acid (as in SEQ ID Nos: 1 and 2) or a glutamic acid residue (GAG) at that position.

A proteolytic fragment corresponding to the N-terminal portion of human BPI holoprotein possesses the antibacterial activity of the naturally-derived 55 kDa human BPI holoprotein. In contrast to the N-terminal portion, the C-terminal region of the isolated human BPI protein displays only slightly detectable anti-bacterial activity. Ooi, et al., *J. Exp. Med.*, 174:649 (1991). A BPI N-terminal fragment designated rBPI$_{23}$, Gazzano-Santoro et al., *Infect. Immun.* 60:4754–4761 (1992), and comprising approximately the first 199 amino acids of the human BPI holoprotein, has been produced by recombinant means as a 23 kD protein.

The bactericidal effect of BPI has been shown to be highly specific for sensitive gram-negative species. The precise mechanism by which BPI kills bacteria is not yet completely elucidated, but it is known that BPI must first attach to the surface of susceptible gram-negative bacteria. This initial binding of BPI to the bacteria involves electrostatic and hydrophobic interactions between the basic BPI protein and negatively charged sites on LPS. LPS has been referred to as "endotoxin" because of the potent inflammatory response that it stimulates, i.e., the release of mediators by host inflammatory cells which may ultimately result in irreversible endotoxic shock. BPI binds to lipid A, the most toxic and most biologically active component of LPS.

In susceptible bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss, *Inflammation: Basic Principles and Clinical Correlates*, eds. Galin et al., Chapter 30, Raven Press, Ltd. (1992)]. BPI is thought to act in two stages. The first is a sublethal stage that is characterized by immediate growth arrest, permeabilization of the outer membrane and selective activation of bacterial enzymes that hydrolyze phospholipids and peptidoglycan. Bacteria at this stage can be rescued by growth in serum albumin supplemented media but not by growth in whole blood, plasma or serum. The second stage, defined by growth inhibition that cannot be reversed by serum albumin, occurs after prolonged exposure of the bacteria to BPI and is characterized by extensive physiologic and structural changes, including penetration of the cytoplasmic membrane.

BPI-induced permeabilization of the bacterial cell envelope to hydrophobic probes such as actinomycin D is rapid and depends upon the initial binding of BPI to LPS, leading to organizational changes which probably result from binding to the anionic groups in the KDO region of LPS, normally responsible for stabilizing the outer membrane through binding of $Mg^{++}$ and $Ca^{++}$. Binding of BPI and subsequent bacterial killing depends, at least in part, upon the LPS polysaccharide chain length, with long O chain bearing organisms being more resistant to BPI bactericidal effects than short, "rough" organisms (Weiss et al., *J. Clin. Invest.* 65: 619–628 (1980). This first stage of BPI action is reversible upon dissociation of the BPI, a process requiring synthesis of new LPS and the presence of divalent cations (Weiss et al., *J. Immunol.* 132: 3109–3115 (1984). Loss of bactericidal viability, however, is not reversed by processes which restore the membrane integrity, suggesting that the bactericidal action is mediated by additional lesions induced in the target organism and which may be situated at the cytoplasmic membrane (Mannion et al., *J. Clin. Invest.* 86: 631–641 (1990)). Specific investigation of this possibility has shown that, on a molar basis, BPI is at least as inhibitory of cytoplasmic membrane vesicle function as polymyxin B (In't Veld et al., *Infection and Immunity* 56: 1203–1208 (1988)) but the exact mechanism has not yet been elucidated.

BPI is also capable of neutralizing the endotoxic properties of LPS to which it binds. Because of its bactericidal properties for gram-negative organisms and its ability to neutralize LPS, BPI can be utilized for the treatment of mammals suffering from diseases caused by gram-negative bacteria, such as bacteria or sepsis.

U.S. Pat. No. 5,198,541 (PCT/US88/02700), the disclosures of which are hereby incorporated by reference, describe recombinant genes encoding and methods for expression of BPI proteins, including BPI holoprotein and fragments of BPI. They also describe the use of N-terminal fragments of BPI protein for co-treatment with certain antibiotics, specifically penicillin, cephalosporins, rifampicin and actinomycin D.

Gram-negative bacteria include bacteria from the following species: Acidaminococcus, Acinetobacter, Aeromonas, Alcaligenes, Bacteroides, Bordetella, Branhamella, Brucella, Calymmatobacterium, Campylobacter, Cardiobacterium, Chromobacterium, Citrobacter, Edwardsiella, Enterobacter, Escherichia, Flavobacterium, Francisella, Fusobacterium, Haemophilus, Klebsiella, Legionella, Moraxella, Morganella, Neisseria, Pasturella, Plesiomonas, Proteus, Providencia, Pseudomonas, Salmonella, Serratia, Shigella, Streptobacillus, Veillonella, Vibrio, and Yersinia species.

Antibiotics are natural chemical substances of relatively low molecular weight produced by various species of microorganisms, such as bacteria (including Bacillus species), actinomycetes (including Streptomyces) and fungi, that inhibit growth of or destroy other microorganisms. Substances of similar structure and mode of action may be synthesized chemically, or natural compounds may be modified to produce semi-synthetic antibiotics. These biosynthetic and semi-synthetic derivatives are also effective as antibiotics. The major classes of antibiotics are (1) the β-lactams, including the penicillins, cephalosporins and monobactams; (2) the aminoglycosides, e.g., gentamicin, tobramycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, and the macrolide antibiotics such as erythromycin and oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, and the tuberculostatic agents isoniazid and para-aminosalicylic acid. Some agents may have more than one primary mechanism of action, especially at high concentrations. In addition, secondary changes in the structure or metabolism of the bacterial cell often occur after the primary effect of the antimicrobial drug.

Heparin is a heterogenous group of straight-chain anionic mucopolysaccharides (glycosaminoglycans) having anticoagulant properties. Although others may be present, the main sugars occurring in heparin are: (1) α-L-iduronic acid 2-sulfate, (2) $^2$-deoxy-2-sulfamino-a-D-glucose 6-sulfate, (3) β-D-glucuronic acid, (4) $^2$-acetamido-2-deoxy-α-D-glucose, and (5) α-L-iduronic acid. These sugars are present in decreasing amounts, usually in the order (2)>(1)>(4)>(3)>(5), and are joined by glycosidic linkages, forming polymers of varying sizes. Heparin is strongly acidic because of its content of covalently linked sulfate and carboxylic acid groups. Hepanin is found within mast cell granules and is released upon degranulation. A cell associated form of heparin is termed heparan sulfate. Heparan sulfate is a broad term used to describe a variety of sulfated proteoglycans (HSPG's) found with a near-ubiquitous distribution on mammalian cell surface membranes and in the extracellular matrix. HSPG contains a variable percentage of pentamaric heparin-like sequences that function in a similar fashion as soluble heparin. The HSPG's serve as a repository for antithrombin III (ATIII) and for heparin-binding growth factors such as fibroblast growth factors (FGF) 1–5, IL-8, GM-CSF and IL-3. Folkman et al., *Inflammation: Basic Principles and Clinical Correlates*, 2d Ed. Chapter 40, pp 821–839 (1992). In fact, cells made genetically deficient in HSPG's require exogenous heparin for growth.

Heparin is commonly administered in doses of up to 400 U/kg during surgical procedures such as cardiopulmonary bypass, cardiac catherization and hemodialysis procedures in order to prevent blood coagulation during such procedures. The anticoagulant effect of heparin in blood is a result of the interaction of heparin with ATIII. The heparin/ATIII complex is a potent inhibitor of many of the clotting factors of the coagulation cascade. Specific inhibition has been demonstrated for activated Factors IXa, Xa, XIa, XIIIa and thrombin. The heparin/ATIII complex has the highest affinity for Factor Xa and thrombin which are common to both the intrinsic and extrinsic clotting pathways involved as the last two steps of the clotting cascade that results in the conversion of fibrinogen to fibrin. The additional antibacterial and antiendotoxin effects of BPI would be particularly advantageous in post-surgical heparin neutralization. When heparin is administered for anticoagulant effects during surgery, it is an important aspect of post-surgical therapy that the effects of heparin are promptly neutralized so that normal coagulation function can be restored.

Angiogenesis is closely associated with endothelial cell proliferation and constitutes the development of new capillary blood vessels. As such, it is an important process in mammalian development and growth, and in menstruation processes. The release of angiogenic growth factors, such as fibroblast growth factors. 1–5, induces proliferation of endothelial cells via a heparin-dependent receptor binding mechanism. See Yayon et al., *Cell*, 64:841–848 (1991). These heparin-binding growth factors can be released due to vascular trauma (wound healing), immune stimuli (autoimmune disease), inflammatory mediators (prostaglandins) and from tumor cells.

Angiogenesis is also associated with a number of pathological conditions in which it would be desirable to inhibit such new blood vessel development. As one example, angiogenesis is critical to the growth, proliferation, and metastasis of various tumors. Other pathological conditions associated with angiogenesis include diabetic retinopathy, retrolental fibroplasia, neovascular glaucoma, psoriasis, angiofibromas, immune and non-immune inflammation including rheumatoid arthritis, capillary proliferation within atherosclerotic plaques, hemangiomas, endometriosis and Kaposi's Sarcoma.

Chronic inflammation is usually accompanied by angiogenesis. Arthritis is a chronic syndrome characterized by the inflammation of the peripheral joints accompanied by synovial thickening and the influx of immune factors and cells such as polymorphonuclear leukocytes (PMN). In rheumatoid arthritis, the inflammation is immune driven, while in reactive arthritis, inflammation is associated with infection of the synovial tissue with pyrogenic bacteria or other infectious agents. Folkman et al., *Inflammation: Basic Prin-* ciples and Clinical Correlates, 2d Ed. Chapter 40, pp 821–839 (1992) note that many types of arthritis progress from a stage dominated by an inflammatory infiltrate in the joint to a later stage in which a neovascular pannus invades the joint and begins to destroy cartilage. While it is unclear whether angiogenesis in arthritis is a causative component of the disease, and not an epiphenomenon, there is evidence that angiogenesis is necessary for the maintenance of synovitis in rheumatoid arthritis.

Co-owned U.S. Pat. No. 5,348,942, continuation-in-part U.S. patent application Ser. No. 08/093,202 filed Jul. 15, 1993 (PCT/US94/02401), continuation-in-part U.S. patent application Ser. No. 08/183,222 filed Jan. 14, 1994 and continuation-in-part U.S. patent application Ser. No. 081209,762 filed Mar. 11, 1994 (PCT/US94/02465) and U.S. patent application Ser. No. 08/306,473 filed Sep. 15, 1994, now U.S. Pat. No. 5,652,332 (PCT/US94/10427), the disclosures of which are hereby incorporated by reference, address use of BPI protein products for treatment of conditions associated with heparin binding and/or neutralition, including neutralization of the anti-coagulant properties of heparin, inhibition of angiogenesis, tumor and endothelial cell proliferation and treatment of chronic inflammatory disease states such as arthritis.

Various other utilities have been described for therapeutic administration of BPI protein products. Co-owned, copending U.S. patent application Ser. No. 08/031,145 filed Mar. 12, 1993 (PCT/US94/02463), and continuation-in-part U.S. patent application Ser. No. 08/285,803 filed Aug. 4, 1994, the disclosures of which are hereby incorporated by reference, address use of BPI protein products in treatment of mycobacterial diseases. Co-owned, copending U.S. patent application Ser. No. 08/125,651, filed Sep.22, 1993, continuation-in-part U.S. patent application Ser. No. 08/273,401 filed Jul. 11, 1994, and continuation-in-part U.S. patent application Ser. No. 08/311,611 filed Sep. 22, 1994, now U.S. Pat. No. 5,523,288 (PCT/US94/11225) address combinations of BPI protein products and antibiotics. Co-owned, copending U.S. patent application Ser. No. 08/273,540 filed Jul. 11, 1994 and continuation-in-part U.S. patent application Ser. No. 08/372,105 filed Jan. 13, 1995, now U.S. Pat. No. 5,627,153 (PCT/US95/00498), the disclosures of which are hereby incorporated by reference, address use of BPI protein products in treatment of fungal infections.

Co-owned, copending U.S. patent application Ser. No. 08/274,299 filed Jul. 11, 1994 and continuation-in-part U.S. patent application Ser. No. 08/372,783 filed Jan. 13, 1995, now U.S. Pat. No. 5,578,572 (PCT/US95/00656), the disclosures of which are hereby incorporated by reference, address use of BPI protein products in treatment of gram-positive infections. Co-owned, copending U.S. patent application Ser. No. 08/132,510, filed Oct. 5, 1993, and continuation-in-part U.S. patent application Ser. No. 08/318,357 filed Oct. 5, 1994 (PCT/US94/11404) address use of BPI protein products in the treatment of conditions involving depressed reticuloendothelial system function. Co-owned, copending U.S. patent application Ser. No. 08/232,527 filed Apr. 22, 1994, now U.S. Pat. No. 5,578,568 addresses use of BPI protein products for treating conditions associated with intestinal ischemia and reperfusion. Co-owned and copending U.S. patent application Ser. No. 08/093,201 filed Jul. 14, 1993, continuation-in-part U.S. patent application Ser. No. 08/274,303 filed Jul. 13, 1994 (PCT/US94/07834) address methods for potentiating BPI protein product bactericidal activity by administration of LBP protein products. Co-owned, copending U.S. patent application Ser. No. 08/188,221 filed Jan. 24, 1994, continuation-in-part U.S. patent application Ser. No. 08/291,112 filed Aug. 16, 1994, now U.S. Pat. No. 5,643,875 and continuation-in-part U.S. patent application Ser. No. 08/378,228 filed Jan. 24, 1995 (PCT/US95/01151) incorporated by reference herein, address use of BPI protein products in the treatment of humans exposed to gram-negative bacterial endotoxin in circulation. The disclosures of all of the patents and patent applications referenced herein are specifically incorporated by reference herein.

Efforts to produce pharmaceutical grade BPI products for human treatment have not yielded uniformly satisfactory results. A principal reason for this is the nature of the amino acid sequence of human BPI and the nature of the recombinant host cell environment in which the products are produced. As one example, biologically-active rBPI products produced as secretory products of CHO host cells transfected with a construct encoding the initial 199 residues of BPI [RBPI (1–199)] may be purified in good yields. As noted in co-owned, copending U.S. patent application Ser. No. 08/072,063, filed May 19, 1993, now U.S. Pat. No. 5,439,807 (PCT/US93/04752) elution of BPI products from S-Sepharose beads incorporated into roller bottles containing transformed CHO cells yielded substantially monomeric BPI products when a 1.0M NaCl-Acetate buffer was employed, but yielded multimeric protein forms when a 1.5M NaCl-Acetate buffer was then employed. Moreover, secreted expression products resulting from CHO cells transfected with DNA encoding a secretory leader sequence and BPI amino acid residues 1–199 actually yielded mixtures of carboxy terminal-shortened BPI protein products terminating at residue 193 or at other residues intermediate between residue 193 and 199. Co-owned, copending U.S. patent application Ser. No. 08/013,801, filed Feb. 2, 1993, now U.S. Pat. No. 5,420,019 (PCT/US94/01235), addresses analog BPI protein products and DNA sequences encoding the same wherein cysteines at positions 132 or 135 are replaced by different amino acids for the purpose of reducing multimer and cysteine adduct formation in recombinant products and also addresses development of recombinant expression products using DNAs encoding the initial amino terminal residue (1) to from about 175 to 193 of BPI, which products display reduced carboxy terminal heterogeneity.

There continues to be a need in the art for improved BPI protein product preparations. Such products would be obtainable in large yield as recombinant products from transformed host cells, would retain the bactericidal, endotoxin binding, endotoxin neutraizing, heparin binding, heparin neutralizing and other biological activities of BPI rendering them suitable for therapeutic use, and would ideally display enhanced in vivo biological activity, thus providing for improved therapeutic methods involving administration of BPI protein products, alone or as a cotreatment with other agents, including, for example, antibiotics.

SUMMARY OF THE INVENTION

The present invention provides significant improvements in therapeutic uses of BPI protein products through the provision of product formulations which include BPI protein products in the form of physiologically stable covalently or non-covalently linked dimeric associations of BPI protein product monomers ("BPI dimers" or "dimeric BPI protein products") which have been discovered to possess enhanced in vivo biological activity in comparison to monomeric product forms. In preferred therapeutic formulations of the invention, dimeric forms of BPI protein products constitute greater than 50 percent by weight of such products. Because of the enhanced in vivo activity of dimeric associations of BPI protein product monomers, product formulations including greater than 75 percent by weight, greater than 90 percent by weight and 95 percent or more by weight dimeric product are successively more preferred.

Therapeutic BPI protein product formulations of the present invention preferably include homodimeric products, but heterodimeric products are also within the contemplation of the invention. Formulations, also preferably include dimeric and, if any, monomeric forms of BPI protein products to the exclusion of higher molecular weight multimer forms such as trimers and the like. Except for formulations or cotreatments developed specifically to include agents that are non-BPI protein products, including, for example, antibiotics and the like as additional active ingredients, formulations or cotreatments according to the invention are substantially free of contaminating materials such as DNA, endotoxin and potentially immunogenic proteins and peptides (including human or recombinant host cell proteins and peptides) which might disqualify the formulations or cotreatments from regulatory acceptance.

The invention also provides uses of a bactericidal/permeability-increasing protein product composition containing greater than 50 percent of a stable covalently or non-covalently linked dimeric product for the manufacture of a medicament for neutralizing endotoxin for the treatment of conditions associated with endotoxin, including exposure to gram-negative bacterial endotoxin in circulation, endotoxemia, gram-negative bacterial infection, mycobacterial infection, and depressed reticuloendothelial cell system function. The invention further provides uses of a bactericidal/permeability-increasing protein product composition containing greater than 50 percent of a stable covalently or non-covalently linked dimeric product for the manufacture of a medicament for neutralizing heparin for the treatment of conditions associated with heparin, including neutralization of the anti-coagulant properties of heparin, inhibition of angiogenesis, inhibition of tumor cell proliferation, inhibition of endothelial cell proliferation, and treatment of chronic inflammatory disease states. Such compositions may be used alone or in co-administration with other agents, including, for example, antibiotic agents. Useful antibiotic agents include (1) the β-lactams, including the penicillins, cephalosporins and monobactams; (2) the aminoglycosides, e.g., gentamicin, tobramycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

The invention also provides improvements in therapeutic uses of BPI protein products including in the therapeutic use of a bactericidal/permeability-increasing protein product to neutralize heparin, the improvement comprising employing a bactericidal/permeability-increasing protein product formulation containing greater than 50 percent of said product in the form of a dimeric product characterized by enhanced in vivo biological activity in comparison to the monomeric form of said product. The invention further provides in the therapeutic use of a bactericidal/permeability-increasing protein product to neutralize endotoxin, the improvement comprising employing a bactericidal/permeability-increasing protein product formulation containing greater than 50 percent of said product in the form of a dimeric product characterized by enhanced in vivo biological activity in comparison to the monomeric form of said product.

The invention further provides improved therapeutic methods involving administration of BPI protein products alone or in co-administration/cotreatment with other agents, including, for example, cotreatment with an antibiotic agent.

Among the preferred dimeric associations of BPI protein products used according to the invention are those developed by means of recombinant expression of DNA sequences encoding amino terminal fragments of BPI, i.e., from the initial amino terminal residue (1) to from about residue 175 to 199, and thereafter processed in a manner promoting disulfide bond linkages between monomers. Specifically preferred are dimeric associations of the recombinant expression products of DNAs encoding residues 1 through 199 and residues 1 through 193 of human BPI (also referred to as "rBPI$_{42}$ dimer"). When expression takes place in, e.g., Chinese Hamster Ovary cells, the possibility of development of expression products having variable carboxy terminal truncations in monomeric forms allows for the generation of dimeric forms wherein the termini of the component monomers may be unequal in length. The use of dimeric forms of amino acid addition, substitution and deletion analog BPI protein products is also contemplated. Analogs involving replacement of a cysteine for example at position 132, with an amino acid incapable of forming a disulfide bond (as in the previously-mentioned U.S. application Ser. No. 08/013,801, now U.S. Pat. No. 5,420,019 (PCT/US94/01235) the disclosures of which are incorporated by reference herein) is not susceptible to dimerization without the use of chemical processes, for example, by means of crosslinking reagents. Analogs wherein cysteines replace amino acids, for example at position 18, or are added to amino or carboxy terminal ends of the BPI protein product will correspondingly be more susceptible to dimerization.

Also, illustrative of formulations of the invention are those containing BPI holoprotein in the form of a dimeric association of protein monomers which are covalently linked by means of disulfide bonds formed between cysteine amino acid residues extant in the BPI protein. Also contemplated are dimeric molecular forms generated through covalent bonding between monomeric forms chemically derivatized by means well known in the art.

The present invention also contemplates the therapeutic use of dimeric BPI protein products formed by the linkage of immunoglobulin portions of BPI-immunoglobulin fusion protein variants such as described in the previously noted U.S. patent applications Ser. Nos. 07/885,911 and 08/064,693, now U.S. Pat. No. 5,643,570 (PCT/US93/04752) the disclosures of which are incorporated by reference herein. It is further within the contemplation of the invention that dimeric BPI protein products be provided as fusion protein products, for example, by analogy with that of single chain antibodies, including, e.g., having a BPI protein product polypeptide at each end of a linear polypeptide, with amino acids providing a spacer or hinge region permitting the BPI polypeptides to assume a dimeric conformation.

BPI protein product formulations of the invention provide for improved therapeutic treatment of gram-negative bacterial infection and the sequels thereof, including conditions associated with gram-negative bacterial endotoxin, such as exposure to gram-negative bacterial endotoxin in circulation, endotoxemia, bacterial and/or endotoxin-related shock and one or more conditions associated therewith, including disseminated intravascular coagulation, anemia, thrombocytopenia, leukopenia, adult respiratory distress syndrome, renal failure, hypotension, fever, and metabolic acidosis. Also contemplated are improved therapeutic treatments of mycobacterial infection (by, e.g., *M. tuberculosis,*

M. leprae and M. avium) and the adverse physiological effects of lipoarabinomannan in circulation according to the methods of previously noted U.S. patent application Ser. No. 08/031,145 (PCT/US94/02463) 08/285,803; treatment of bacterial infections and the sequelae thereof by concurrent treatment with antibiotics according to the methods of previously noted U.S. patent application Ser. Nos. 08/125, 651, 08/273,401, 08/311,611, now U.S. Pat. No. 5,523,288 (PCT/US94/11225); treatment of gram-positive bacterial infections according to the methods of previously noted U.S. patent application Ser. Nos. 08/274,299 and 08/372,783, now U.S. Pat. No. 5,578,572 (PCT/US95/00656); treatment of fungal infections according to the methods of previously noted U.S. U.S. patent application Ser. Nos. 08/275,540 and 08/372,105, now U.S. Pat. No. 5,627,153 (PCT/US95/00498); treatment of depressed reticuloendothelial cell system function according to the methods of previously noted U.S. patent application Ser. Nos. 08/132,510 and 08/318,357 (PCT/US94/11404); and treatment of conditions associated with intestinal ischemia and reperfusion according to the methods of previously noted U.S. patent application Ser. No. 08/232,527, now U.S. Pat. No. 5,578,568, the disclosures all of which are incorporated by reference herein.

Improvements of the invention also apply to therapeutic methods for the use of dimeric BPI protein products as heparin neutralizing agents for treatment of conditions not directly associated with gram-negative bacterial infection, including neutralization of the anti-coagulant properties of heparin, inhibition of angiogenesis, inhibition of tumor cell proliferation, inhibition of endothelial cell proliferation and treatment of chronic inflammatory disease states such as arthritis according to the disclosures of previously noted U.S. patent applications Ser. Nos. 08/030,644, now U.S. Pat. No. 5,348,942, 08/093,202, 08/183,222, 08/209,762 and 08/306,473, now U.S. Pat. No. 5,652,332 the disclosures of which are hereby incorporated by reference.

The invention thus contemplates that administration of BPI protein product dimers will provide beneficial activity for neutralizing heparin, including neutralizing the anti-coagulant activity of heparin when administered in vivo to a subject. It is also contemplated that such products will be particularly useful when administered to subjects in order to inhibit endothelial cell proliferation and angiogenesis associated with a variety of conditions including malignant tumor proliferation, Kaposi's sarcoma lesions and the like. Cancers susceptible to treatment by administration of dimeric BPI protein products include melanoma, sarcomas, and carcinomas including, but not limited to, breast, colon, lung and prostate carcinomas. Other conditions for which dimeric BPI protein products can be administered for inhibition of angiogenesis include ocular retinopathy, retrolental fibroplasia, psoriasis, angiofibromas, endometriosis, hemangiomas and the like. Also contemplated by the invention are uses of dimeric BPI protein products in methods of contraception comprising delivering of an effective amount of a BPI protein product so as to prevent implantation of a fertilized ovum, methods of treating chronic inflammatory disease states such as arthritis, psoriasis, inflammatory bowel disease, Crohn's disease, ulcerative colitis, lupus erythematosus, autoimmune uveitis, Lyme disease, and asthma.

Antimicrobial therapeutic methods of the present invention may involve administration of dimeric BPI protein products alone or in co-administration or concurrent treatment with antibiotic agents according to the disclosures of previously noted U.S. patent application Ser. Nos. 08/125, 651, 08/273,401, 08/311,611, now U.S. Pat. No. 5,523,288 (PCT/US94/11225), 08/031,145 (PCT/US94/02463) and 08/285,803 incorporated by reference herein.

Also provided according to the present invention are novel methods for preparing compositions comprising high proportions of dimeric forms of BPI protein products, especially recombinant products, suitable for pharmaceutical use and characterized by being substantially free of multimeric BPI protein products, human or host cell proteins or peptides, polynucleotides and endotoxin. According to one illustrative method, recombinant dimeric BPI protein products can be recovered from recombinant host cell fermentation by contact one or more times with a first cationic exchange resin (e.g., SP-Sepharose) and elution therefrom under suitable pH and sodium chloride salt concentrations (e.g., Ph 4.0 and 1.5M NaCl), followed by contact with a second cationic exchange resin (e.g., CM-Sepharose), removal of BPI protein product monomer with a 0.5M NaCl solution at pH 4.0 and elution with a 1.0M NaCl solution at pH 4.0 to provide a BPI protein product dimer-containing eluate, followed by contact with and elution from a size exclusion resin (e.g., Sephacryl S-100) under suitable pH and salt concentration (e.g., pH 5.0 and 0.15M NaCl) to provide compositions comprising about 99% pure, dimeric BPI protein product suitable for use in pharmaceutical formulations.

According to another illustrative method, monomeric BPI protein product compositions are converted in solution with copper ions, particularly cupric ($Cu^{++}$), ions to provide compositions having high proportions of dimeric products. Solutions containing BPI protein products in substantially monomeric form are contacted with cupric ion in appropriate concentrations (e.g., 2 $\mu$M to 100 $\mu$M), at suitable pH (e.g., from about pH 5.0 to about pH 9.0), with or without pretreatment with suitable reducing agents such as dithiothriitol for elimination of cysteine adducted monomer forms, to provide compositions with 85% or more dimeric molecular species without reduction or 95% or more with reduction. Use of cupric ion to promote dimer formation is preferably carried out in the absence of chelating agents such as EDTA or citrate ion which tend to inactivate the cupric ion. Applied to recovery of recombinant dimeric BPI protein products from host cell fermentation, cupric ion catalyzed conversion of product monomers to dimeric forms is performed as an intermediate step in a total recovery process which can include preliminary steps of contact with and elution from a first cationic resin (e.g., SP-Sepharose) under pH and salt concentrations selected to minimize elution of dimeric and multimeric product forms (e.g., pH 4.0 and 1.0M NaCi), contact with and elution from a second cationic exchange resin (e.g., CM-Sepbarose, wash at 0.35M NaCl and elute at 0.60M NaCl) under functionally comparable elution conditions together with optional reducing and viral inactivation steps. Recovery procedures following cupric ion conversion to dimeric forms can include application to a third cationic exchange resin (e.g., CM-Spherodex) under suitable pH and salt concentration conditions (e.g., pH 5.0 and 0.5M NaCl to remove nonconverted monomer and at 1.0M NaCl to elute dimer) followed by contact with and elution from a size exclusion resin (e.g., Sephacryl S-100) under suitable pH and salt concentration conditions (e.g., pH 5.0 and 0.15M NaCl).

Numerous additional aspects and advantages of the invention will become apparent to those skilled in the art upon considering the following detailed description of the invention which describes presently preferred embodiments thereof, reference being made to the drawing wherein:

DETAILED DESCRIPTION

Figure 1:
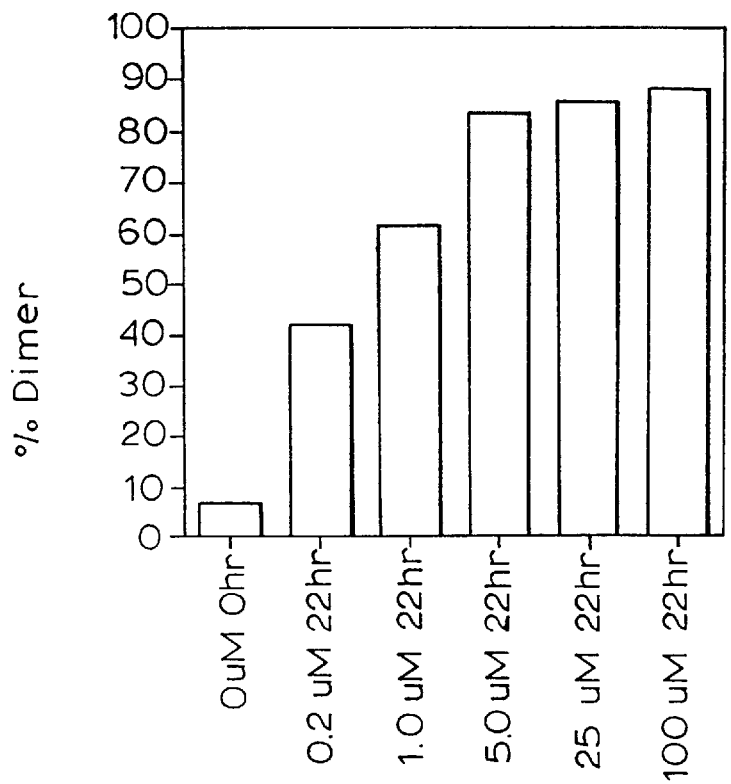
FIG. 1 depicts the effect of $CuSO_4$ concentration on conversion of BPI monomer to BPI dimer.

As used herein, "BPI protein product" includes naturally and recombinantly produced bactericidal/permeability-increasing protein; natural, synthetic, and recombinant biologically active polypeptide fragments of bactericidal/permeability-increasing protein; and biologically active polypeptide analogs, including hybrid fusion and variant proteins, of either bactericidal/permeability increasing protein or biologically active fragments thereof. BPI protein products including biologically active fragments of BPI holoprotein administered according to the methods of this invention may be generated and/or isolated by any means known in the art. For example, U.S. Pat. No. 5,198,541, the disclosure of which is hereby incorporated by reference, describes recombinant methods and materials for expression of BPI proteins products. It also describes the use of N-terminal fragments of BPI protein for cotreatment with certain antibiotics, specifically penicillin, cephalosporins, rifampicin and actinomycin D.

The following detailed description relates to the development and properties of illustrative rBPI protein product formulations according to the invention and particularly those comprising dimeric forms of monomeric products based on amino terminal fragments of BPI.

In particular, the detailed description illustrates preparative methods for the isolation of BPI protein product dimers from heterogeneous preparations containing monomeric, dimeric and/or other molecular forms such as cysteine adducted forms and methods for the conversion of BPI in monomeric or cysteine adduct form into BPI dimers.

Methods for the separation of BPI protein product dimers from heterogeneous BPI preparations include use of chromatographic separation techniques. According to one method, the growth medium of transformed mammalian cells producing a BPI protein product is contacted with cation exchange materials such as S-Sepharose or SP-Sepharose. The cation exchange materials are washed with a weak buffer such as 0.65M NaCl-Acetate to remove some impurities and a stronger buffer such as 1.0M NaCl-Acetate to elute monomeric products from the exchange materials, leaving behind dimers and multimers of the BPI protein product on the cation exchange material. Dimers and multimers may then be eluted with an even stronger buffer such as 1.5M NaCl-Acetate. Further separations may be practiced to remove contaminants such as DNA from the 1.5M NaCl-Acetate eluate and to separate dimeric from multimeric forms. For example, separation of DNA from BPI protein products can be carried out at pHs of about 4.0.

Dimeric products isolated from fermentation media of cells transformed with a DNA encoding the BPI signal sequence and the amino-terminal 199 residues of BPI tend to be homogeneous with respect to length of the polypeptide monomeric subunits involved in formation of the dimers. While monomeric products isolated from such fermentation media display a variety of different terminal residues, with the predominant monomeric species having residues 1–193, the dimeric forms isolated directly from fermentation by chromatographic procedures tend to predominantly include monomeric subunits having residues 1–199, suggesting that dimer formation in the host cells or the medium "protects" the product from carboxy terminal degradation. Conversion of BPI protein product monomers to dimeric forms in vitro by copper sulfate catalyzed dimerization of isolated monomers leads to recovery of products predominantly including dimers formed from monomers having residues 1–193. Such amino-terminal dimers (e.g., 1–199 or 1–193) are also designated rBPI$_{42}$ dimers or rBPI$_{42}$.

While BPI protein product monomers will gradually dimerize in solution, such conversion is very slow and is commercially impractical. The oxidation reaction for rBPI$_{23}$ proceeds slowly at pH 5 (resulting in approximately 15% conversion to dimer in one year). The presence of cupric ($Cu^{2+}$) ions substantially accelerates conversion of monomer to dimer.

The utility of $Cu^{2+}$ ions to efficiently accelerate formation of biologically active BPI protein product dimers is surprising in light of the disclosures of Engleka et al., *J. Biol. Chem.* 267: 11307–11315 (1992) which notes that copper-oxidized dimerization of human FGF-1 proceeds efficiently to generate products which no longer possess either mitogenic biological activity or heparin binding capacity, but that similar quantitative dimerization by cupric ion oxidation did not occur when structurally analogous bovine FGF-1 and recombinant human FGF-2 were treated.

The formation of cysteine adducts in a heterogeneous BPI protein product mixture can significantly limit the yield of BPI protein product dimers because such cysteine adducts will not dimerize, even in the presence of cupric ion. In certabi cases, the product of a cell culture fermenter may consist of BPI dimer and cysteine adduct with essentially no non-adducted BPI monomer. According to one aspect of the invention, cysteine adducts in a heterogenous BPI protein product mixture can be reduced to form non-adducted product monomers prior to conversion to dimeric form. For example, if BPI is first reduced to eliminate cysteine adducts, about 90% or more of the monomer can be converted by copper sulfate. Conversions can be significantly less over a given time period where cysteine adducts are not so reduced (i.e., about 80% or more in 5 hours). Accordingly, a reducing agent such as dithiothreitol (DTT) may be added to heterogeneous mixtures of dimers, monomers and cysteine adducts in order to produce BPI protein monomer which is then converted to dimer in high yields. It is contemplated that other reducing agents such as Tris(2-carboxyethyl)phosphine (TCEP) will be equally useful in the reduction of cysteine-adducts.

A variety of factors will influence the overall formation and yield of dimer. Accordingly, those of skill in the art will know to balance the effects of product losses with conversion rates in order to maximize ultimate yields. The oxidation of BPI protein product monomer to produce dimer is likely a second order reaction with respect to BPI concentrations. For example, increases in BPI protein product concentration will increase the dimer formation rate at any given reaction pH. While the dimer formation rate generally increases with increasing pH, product yield may be decreased at higher pHs due to protein insolubility or loss. The dimer formation rate is also dependent upon the concentration of $Cu^{2+}$ ion with concentrations of from about 2 $\mu M$ to about 100 $\mu M$ $Cu^{2+}$ being preferred. Lower concentrations are less effective at promoting the dimerization reaction. The rate of dimerization is also a function of temperature. Specifically, dimer formation occurs more rapidly at room temperature than at 4° C. although protein stability may be greater at the reduced temperature. Buffer selection may also influence dimer formation. However, experiments comparing Tris and phosphate buffers found no significant difference between the two with respect to rate of dimer formation or the ultimate percentage of dimer recovered. On the other hand, the incorporation of citrate buffer has the effect of chelating the $Cu^{2+}$ ion and will substantially reduce the rate of dimerization. Similarly, high concentrations of phosphate may have the effect of precipitating cupric ion. Variations in NaCl concentrations ranging from 0.1 to 1.7M NaCl did not substantially affect dimer yields.

As one aspect of the invention it has been found that cationic exchange resins such as those used in the purification procedures of the invention or in the improved cell culture methods of co-owned and copending U.S. Ser. No. 08/072,063 filed May 19, 1993 (PCT/US94/04752) may promote BPI protein product dimer formation by means of physical or charge interactions. Accordingly, dimer formation can be efficiently carried out in the cell culture fermenter and/or on the media of cationic exchange purification columns. To the extent that it is desired to promote dimer formation in the cell culture fermenter it may be desirable to alter the concentration of cationic exchange resin in the fermenter in order to influence dimer formation. In addition, the cupric ion concentration of the cell culture fermentation media can be increased in order to promote dimer formation in that media. Further, it may also be desirable to reduce the cysteine or cystine concentration of the fermentation media in order to repress formation of cysteine adducts. Nevertheless, such cysteine concentrations should not be so reduced as to be rate limiting for cell growth.

The administration of BPI dimers is preferably accomplished with a pharmaceutical composition comprising the product and a pharmaceutically acceptable diluent, adjuvant or carrier. The BPI protein product composition may be administered without or in conjunction with known antibiotics, surfactants or other chemotherapeutic agents. A preferred pharmaceutical composition comprises the BPI protein at a concentration of 1 mg/ml in citrate buffered saline (0.02M citrate, 0.15M NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Such preferred combinations are taught in co-owned, copending U.S. patent application Ser. No. 08/012,360 filed Feb. 2, 1993, continuation-in-part Ser. No. 08/190,869 filed Feb. 2, 1994 (PCT/US94/01239), and continuation-in-part Ser. No. 08/251,576 the disclosures of which are herein incorporated by reference. Also of interest is the disclosure, incorporated herein by reference, of co-owned, copending U.S. patent application Ser. No. 08/372,104 relating to improved therapeutic compositions of BPI.

The BPI protein product can be administered by any known method, such as orally, systemically (such as by intravenous, intramuscular or other injection), or as an aerosol. Medicaments can be prepared for oral administration or by injection or other parenteral methods and preferably include conventional pharmaceutically acceptable carriers and adjuvents as would be known to those of skill in the art. The medicaments may be in the form of a unit dose in solid, semi-solid and liquid dosage forms such as tablets, pills, powders, liquid solutions or suspensions, and injectable and infusible solutions. Effective dosage ranges from about 100 $\mu g/kg$ to about 100 mg/kg of body weight are contemplated.

The present invention will be better understood upon consideration of the following illustrative examples wherein: Example 1 relates to construction of vectors for expression of BPI protein products; Example 2 addresses the incorporation of vectors of Example 1 into appropriate host cells for the expression of preferred BPI protein product polypeptides; Example 3 relates to methods suitable for the isolation of dimeric products from the medium of CHO cells transfected with DNA encoding the secretory signal and BPI residues 1–199; Example 4 relates to evaluation of various divalent metal ions for promotion of dimer formation; Example 5 relates to methods for the conversion to dimeric forms; Example 6 relates to methods for the purification and conversion to dimeric products; Example 7 describes evaluation of BPI protein products including dimer-containing formulations in a rat LPS infusion (experimental endotoxemia) model; Example 8 relates to evaluation of BPI protein products including dimer-containing formulations in a rabbit endotoxemia model; Example 9 relates to the activity of monomeric BPI protein products in a rat LPS infusion model; Example 10 relates to the efficacy of BPI protein product dimer-containing formulations in a mouse acute peritonitis model; Example 11 relates to the effect of BPI dimer in a mouse endotoxemia model; Example 12 relates to the pharmacokinetics of dimer-containing formulations in rats; Example 13 relates to the ability of BPI protein product formulations including dimeric molecular forms prebound to human umbilical vein endothelial (HUVEC) cells to bind LPS; Example 14 relates to quantification of heparin binding by BPI dimer; Example 15 related to the effect of BPI dimer on heparin-mediated lengthening of thrombin time; Example 16 relates to the effect of dimer-containing formulations on heparin-mediated lengthening of partial thromboplastin time in vitro and in vivo; and Example 17 relates to the effect of dimer-containing formulations on heparin neutralization in a Matrigel™ model of angiogenesis.

EXAMPLE 1

Construction Of Vectors For Expression of rBPI$_{21}\Delta$cys and Optimized Vectors For Expression of rBPI (1–193)

In this example, construction of vectors for expression of a variety of BPI protein products including the product of expression of a DNA encoding residues 1–193 of BPI wherein the cysteine at position 132 is replaced by alanine (referred to herein as rBPI₂Δcys) and the product of expression of a DNA encoding residues 1–193 of BPI (referred to herein as rBPI (1–193) and the product of expression of DNA encoding residues 1–199 of BPI (referred to herein as rBPI₂₃) are disclosed. The rBPI (1–193) product is a presently preferred source of monomer for preparation of dimeric BPI protein products for practice of the invention.

A. Construction Of Plasmids pING4519 And pING4520

The expression vector, pING4503, was used as a source of DNA encoding a recombinant expression product designated rBPI (1–199), i.e., encoding a polypeptide having the 31-residue signal sequence and the first 199 amino acids of the N-terminus of the mature human BPI, as set out in SEQ ID NOs: 1 and 2 except that valine at position 151 is specified by GTG rather than GTC and residue 185 is glutamic acid (specified by GAG) rather than lysine (specified by AAG).

Plasmid pING4503 has been described in co-pending, co-owned U.S. patent application Ser. No. 071885,911 by Theofan, et al. which is incorporated herein by reference with respect to the background of the invention. Briefly, the construction of pING4503 is based on plasmid pING2237N which contains the mouse immunoglobulin heavy chain enhancer element, the LIR enhancer-promoter element from Abelson murine leukemia virus (A-MuLv) DNA, the SV40 19S/16S splice junction at the 5' end of the gene to be expressed, and the human genomic gamma-1 polyadenylation site at the 3' end of the gene to be expressed. Plasmid pING2237N also has a mouse dihydrofolate reductase (Dsi) selectable marker. The DNA encoding rBPI (1–199), including 30 bp of the natural 5' untranslated region and bases encoding the 31 amino acid signal sequence, as well as 199 N-terminal amino acids of BPI, is inserted between unique SalI and SsII restriction sites in pING4503.

Two vectors, pING4519 and pING4520, were constructed based on pING4503 for expression of rBPI (1–199) cysteine replacement analogs in which one of the three naturally-occurring cysteine residues of BPI was replaced with another amino acid. A PvuII site (CAGCTG) which occurs only once in the DNA encoding rBPI (1–199), and which is located between cysteine 132 and cysteine 135, was utilized in these constructions. Because several additional PvuII sites exist in pING4503, it was first necessary to isolate the SalI-SstII fragment which contained the insert encoding rBPI (1–199) from pING4503 by digesting with SalI and SstII. The purified SalI-SstII rBPI (1–199) insert was then digested with PvuII, resulting in an approximately 529 bp SalI-PvuII fragment and an approximately 209 bp PvuII-SstII fragment, each of which was purified separately.

Plasmid pING4519 is identical to pING4503 except that pING4519 contains a DNA insert encoding an rBPI (1–199) in which a codon for alanine is substituted for the codon specifying the native cysteine at position 132. The recombinant product resulting from host cell expression and secretory processing of such an insert is referred to as "rBPI (1–199) ala¹³²." In order to generate pING4519, BPI DNA sequences were PCR amplified from pING4503 using the primers BPI-6: AAGCTRGTCGACCAGGCCTTGAGGT (SEQ ID NO: 3), which incorporated a SalI restriction site at the 5' end of the 30 bp BPI untranslated region, and BPI-14: CTGGAGGCGGTGATGGTG (SEQ ID NO: 4), which incorporated one half of the PvuII site and the base substitutions necessary to code for alanine at position 132. PCR amplification was accomplished using the GeneAmp PCR kit (Perkin Elmer Cetus, Norwalk, Conn.) according to the manufacturer's instructions. The resulting PCR fragment was digested with SalI, resulting in an approximately 529 bp SalI-blunt fragment which was then used in a three-piece ligation, together with the approximately 209 bp PvuII-SstII fragment described above and the large fragment resulting from SalI and SstII digestion of pING4503, to generate pING4519.

Plasmid pING4520 is identical to pING4519 with the exception that pING4520 contains a DNA insert encoding an rBPI (1–199) analog in which a serine codon is substituted for the codon specifying the native cysteine at position 135. The recombinant product resulting from host cell expression of such an insert is designated "rBPI (1–199) ser¹³⁵". In order to generate pING4520, BPI DNA sequences were PCR amplified from pING4513, a plasmid essentially similar to pING4503 except that the selection marker is gpt instead of Dow and the cDNA insert encodes the signal sequence and full-length BPI (456 residues) instead of only the rBPI (1–199) portion.

Amplification by PCR was accomplished using primer BPI-15: CTCCAGCAGCCACATCAAC (SEQ ID NO: 5), wherein the 5' end incorporates one half of a mutated PvuI site (wherein "CTG" is changed to "CTC") and the base substitutions necessary to code for serine at position 135; and primer BPI-7: GAACITGGTTGTCAGTCG (SEQ ID NO: 6), representing rBPI-encoding sequences located downstream of the region encoding BPI residue 199. This PCR fragment was digested with BstBI, which cuts downstream of the cysteine 135 mutagenesis site, and the resulting approximately 100 bp blunt-BstBI fragment was gel purified. A three piece ligation was then performed with the 529 bp SalI-PvuII BPI restriction fragment described above, the 100 bp blunt-BstBI fragment, and a large fragment resulting from BstBI-SalI digestion of pING4503, to generate pING4520.

B. Construction Of Plasmid pING4530

Another vector, pING4530, was constructed which contained the alanine-for-cysteine replacement as in pING4519, but which contained the gpt selectable marker (allowing for mycophenolic acid resistance) instead of the DHFR marker carried over from pING4503 to pING4519. To construct pING4530, a 1629 bp SalI-DraIII restriction fragment was isolated from pING4519. This fragment included all of the rBPI (1–199) ala¹³² coding region as well as an additional approximately 895 bp vector sequence at the 3' end of the coding region. This fragment was ligated to the large (approximately 7230 bp) DraIII-SalI vector fragment isolated from pING4513 to generate pING4530.

C. Construction Of Plasmid pING4533

Plasmid pING4533 was constructed for expression of rBPI (1–199) ala¹³², wherein the codon specifying the fifth amino acid of the BPI signal sequence, methionine (ATG), at position −27 was placed in the context of the consensus Kozak translation initiation sequence GCCACCRCCATGG (SEQ ID NO: 7) [Kozak, Nucl. Acid. Res., 15:8125 (1987)], and in which the DNA sequence encoding the first 4 amino acids of the BPI signal was removed. This was accomplished by PCR amplification of BPI sequences from a plasmid containing the full length human BPI cDNA [in pGEM-7zf (+)] using the PCR primer BPI-23: ACTGTCGACGCCAC-CATGGCCAGGGGC (SEQ ID NO: 8), incorporating a SalI restriction site and the nucleotides GCCACC in front of the ATG (methionine) at position −27 of the BPI signal, and the primer BPI-2: CCGCGGCTCGAGCTATATTTTGGTCAT (SEQ ID NO: 9), corresponding to the 3' end of the rBPI (1–199) coding sequence.

The approximately 700 bp PCR amplified DNA was digested with SalI and EcoRI and the resulting 270 bp fragment, including approximately the first one-third of the BPI (1–199) coding sequence, was purified. This SalI-EcoRI fragment was ligated to 2 other fragments: (1) a 420 bp EcoRI-SstII fragment from pING4519, encoding the remainder of BPI (1–199) wherein alanine replaces cysteine at position 132; and (2) an approximately 8000 bp SstII-SalI vector fragment from pING4502 (a vector essentially similar to pING4503 except that it does not include the 30 bp 5' untranslated sequence and has a gpt marker rather than DHFR), to generate pING4533 which contains a gpt marker.

D. Construction Of Plasmids pING4221. pING4222. And pING4223

Vectors similar to pING4533 were constructed having an insert which contained the optimized Kozak translation initiation site corresponding to methionyl residue −27 of the signal sequence, and an alanine-for-cysteine replacement at position 132. However, the BPI fragment coding sequence terminated at residue 193 in these constructions. The recombinant product resulting from host cell expression of this DNA is referred to as "rBPl (1–193) ala$^{132}$" or as "rBPI$_{21}$Δcys." Vectors containing these inserts were made by first digesting pING4533 with SalI, which cuts at the 5' end of the BPI DNA insert, and AlwNI, which leaves a three bp 3'-overhang at residue 192. The resulting approximately 700 bp fragment was then purified. This fragment was re-ligated into the large fragment resulting from pING4533 digestion with SstII-SalI, along with two annealed complementary oligonucleotides, BPI-30: CTGTAGCTCGAGC-CGC (SEQ ID NO: 10) and BPI-31: GGCTCGAGCTACA-GAGT (SEQ ID NO: 11). This replaced the region between the AlwNI and SstII sites with the codon for residue 193 (leucine), a stop codon, and an XhoI restriction site 5' to the SstII site and resulted in regeneration of both the AlwNI and the SstII sites and placement of the stop codon, TAG, immediately after the codon (CTG) for amino acid 193 (leucine). The resultant plasmid was designated pING4223 and had the gpt marker. Similar constructions were made exactly as described for pING4223 except that different SstII-SalI vector fragments were used to generate vectors with different selection markers. For example, pING4221 is identical to pING4223 except that it contains the his marker (conferring resistance to histidinol) instead of gpt and pING4222 is identical to pING4223 except that it contains the DHFR marker instead of gpt.

E. Construction Of Plasmids pING4537, pING4143, pING4146, pING4150, And pING4154

A series of vectors was constructed which contained an insert encoding rBPI (1–193) ala$^{132}$, the optimized Kozak translation initiation site, and different selection markers essentially identical to those described with respect to pING4221, pING4222 and pING4223 except that the human genomic gamma-1 heavy chain polyadenylation and transcription termination region at the 3' end of the SstII site was replaced with a human light chain polyadenylation sequence followed by mouse light chain (kappa) genomic transcription termination sequences. In collateral gene expression studies, the light chain polyadenylation signal and transcription termination region appeared to be responsible for 2.5–5 fold increases in BPI expression levels in Sp2/0 and CHO-K1 cells.

The aforementioned vectors were constructed by first constructing pING4537, a vector similar to pING4533 which contains the rBPI (1-199) ala$^{132}$ insert. However, pING4537 includes the human light chain polyadenylation and mouse kappa genomic transcription termination sequences instead of the human heavy chain sequence. These 3' sequences were obtained from pING3170, an expression vector which encodes a human light chain cDNA and includes a mouse genomic light chain 3' transcription termination sequence. This was accomplished by digesting with SstI, which cuts 35 bp upstream of the human stop codon, treating with T4 DNA polymerase to make the end blunt, then cutting with BamHI, and purifying an approximately 1350 bp fragment which includes the mouse kappa 3' sequences. The resulting fragment consists of approximately 250 bp of the 3' portion of the human light chain constant region cDNA and the polyadenylation signal followed by a BamHI linker as described in the construct called Δ8 in Lui et al., *J. Immunol.* 139: 3521, (1987). The remainder of the approximately 1350 bp fragment consists of a BglII-BamHI mouse kappa 3' genomic fragment [fragment "D" of Xu et al., *J. Biol. Chem.* 261:3838, (1986)] which supplies transcription termination sequences. This fragment was used in a 3-piece ligation with two fragments from pING4533: a 3044 bp fragment which includes all of BPI insert and part of vector obtained by digestion with SstII, T4 polymerase treatment, and NotI digestion (which includes all of BPI insert and part of vector), and an approximately 4574 bp BamHI-NotI fragment. The resulting vector, pING4537, is identical to pING4533 with the exception of the above-noted differences in the genomic 3' untranslated region.

Additional vectors containing the kappa 3' untranslated sequences were constructed using pING4537 as the source of the kappa 3' fragment. The kappa 3' untranslated sequences were isolated by digestion of pING4537 with XhoI (a unique site which occurs immediately after the BPI stop codon) and BamHI. The resulting approximately 1360 bp XhoI-BamHI fragment was used in a series of 3-piece ligations to generate the following four vectors, all of which have inserts encoding rBPI (1–193) ala$^{132}$ and which have the optimized Kozak translation initiation site at residue −27 of the signal: (1) pING4143 (gpt marker), obtained by ligating a pING4223 4574 bp BamHI-NotI fragment (gpt marker), a pING4223 NotI-XhoI BPI insert-containing fragment of approximately 3019 bp, and the pING4537 XhoI-BamHI fragment; (2) pING4146 (DHFR marker), obtained by ligating a pING4222 approximately 4159 bp BamHI-NotI fragment (DHFR marker), a pING4223 NotI-XhoI BPI insert-containing fragment of approximately 3019 bp, and the pING4537 XhoI-BamHI fragment; (3) pING4150 (his marker), obtained by ligating a pING4221 his-containing approximately 4772 bp BamHI-NotI fragment, a pING4222 NotI-XhoI BPI insert-containing fragment, and the pING4537 XhoI-BamHI fragment; and (4) pING4154 (neo marker), obtained by ligating a pING3174 neo-containing approximately 4042 bp BamHI-BsaI fragment, a pING4221 BsaI-XhoI BPI insert-containing fragment of approximately 3883 bp and the pING4537 XhoI-BamHI fragment. Plasmid pING3174 contains an insert encoding antibody heavy chain DNA and has a neo marker. The neo gene and its flanking sequences were obtained from the pSv2 neo plasmid reported by Southern et al., *J. Mol. Appl. Genet.,* 1:327 (1982).

F. Construction Of Plasmids pING4144 And pING4151

Figure 3:
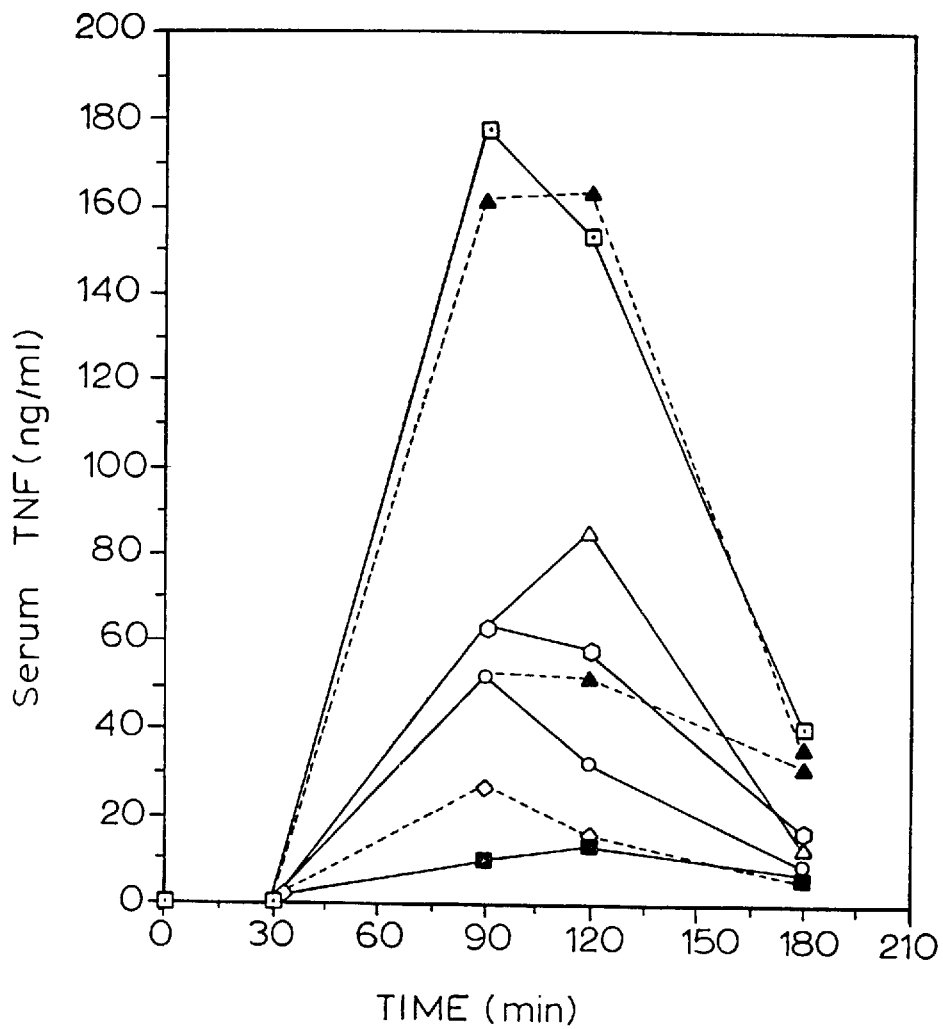
FIG. 3 depicts the effects of BPI protein products on TNF levels in a rat LPS infusion endotoxemia model.

Two plasmids were constructed, pING4144 and pING4151, which were identical to pING4143 and pING4150, respectively, except that expression of rBPI coding sequences was under control of the human cytomegalovinis (hCMV) immediate early enhancer/promoter instead of the Abelson murine leukemia virus (A-MuLv) LTR promoter. Therefore, both pING4144 and pING4151 contained the mutation of the cysteine at position 132 to alanine, the optimized Kozak translation initiation sequence, and the human light chain poly-A/mouse kappa genomic transcription termination region. The region between nucleotides 879 and 1708 of the original vectors (pING4143 and pING4150) was replaced with a region of the hCMV enhancer/promoter corresponding to nucleotides −598 through +174 as shown in FIG. 3 of Boshart et al., *Cell* 41:521 (1985), incorporated herein by reference. To introduce the hCMV promoter region into BPI expression vectors, plasmid pING4538 was first constructed by replacing the approximately 11 17 bp EcoRI-SalI/A-MuLv promoter-containing fragment of pING4222 with an approximately 1054 bp EcoRI-SalI/hCMV promoter-containing fragment from plasmid pING2250 which contains the hCMV promoter driving expression of an antibody light chain insert. To construct pING4144, three fragments were ligated together: (1) the approximately 2955 bp rBPI (1–193)-containing NotI-XhoI fragment from pING4538; (2) the approximately 1360 bp XhoI-BamHI fragment from pING4537; and (3) the approximately 4770 bp BamHI-NotI fragment containing the his gene from pING4221.

G. Construction Of Plasmids pING4145, pING4148 And pING4152

Plasmids pING4145, pING4148 and pING4152 were constructed and were identical to pING4143, pING4146, and pING4150, respectively, except that they contained the natural sequence cysteine at position 132 instead of an alanine substitution. Thus, all three contained the rBPI (1–193) insert, the optimized Kozak translation initiation sequence and the human light chain Poly A/mouse kappa genomic transcription termination region. These three plasmids were constructed as follows. To construct pING4145, three fragments were ligated together: (1) the approximately 3000 bp NotI-XhoI BPI (1–193) containing fragment from pING4140 (pING4140 is identical to pING4221 except that it contains the natural sequence cysteine at Position 132); (2) the approximately 1360 bp XhoI-BamHI fragment from pING4537; and (3) the approximately 4570 bp BamHI-NotI fragment containing the gpt gene from pING4223. To construct pING4148, three fragments were ligated together: (1) the NotI-XhoI fragment from pING4140; (2) the XhoI-BamHI fragment from pING4537; and (3) the approximately 4150 bp BamHI-NotI fragment containing the DH gene from pING4222. To construct pING4152, three fragments were ligated together: (1) the approximately 3000 bp NotI-XhoI fragment from pING4142 (pING4142 is identical to pING4223 except that it contains the natural sequence cysteine at 132); (2) the XhoI-BamHI fragment from pING4537; and (3) the approximately 4770 bp BamHI-NotI fragment containing the his gene from pING4221.

H. Construction Of Plasmids pING4147 pING4153, pING4149 And pING4063

Four plasmids incorporating different selection markers were constructed for expression of BPI (1–193) in the optimized expression vectors. These vectors all included the CMV promoter, the optimized Kozak translation initiation sequence at position −27 of the signal peptide, and the human kappa poly A/mouse kappa genomic transcription termination sequences. These four plasmids, whose construction are described below, are: pING4147 (gpt), pING4153 (his), pING4149 (DHFR) and pING4063 (neo).

pING4147, containing the gpt marker, is identical to pING4145 (Table I) except that it contains the CMV promoter instead of the A-MuLV promoter. pING4147 was constructed by ligating three fragments together: the ~6000 bp BstBI-NotI vector fragment of pING4144 (Table I) containing the light chain 3' sequences and the gpt marker, the ~1900 bp NotI-SalI fragment of pING4144 containing the CMV promoter region, and the ~600 bp SalI-BstBI BPI-containing fragment of pING4142. pING4142 is identical to pING4145 (Table I) except that it contains the human genomic heavy 3' sequences instead of the light chain 3' sequences.

pING4153, which contains the his marker, was constructed by ligating three fragments together: the ~4000 bp BamHI-NotI fragment of pING4221 (Table I) containing the his marker, the ~2700 bp NotI-XhoI fragment of pING4147 (described above) containing the CMV promoter and BPI insert sequences, and the ~1300 bp XhoI-BamHI fragment of pING4537 (described in section 1E) containing the light chain 3' sequences.

pING4149, which contains the DHFR gene for selection, was constructed by ligating these two fragments together: the ~5900 bp XhoI-NotI vector fragment of pING4540 including the DHFR gene, and the ~2700 bp NotI-XhoI fragment of pING4147 (described above) containing the CMV promoter and BPI insert sequences. pING4540 is identical to pING4144 (Table I) except that it contains the DHFR gene instead of gpt for selection.

pING4063 is identical to pING4147 (described above) except that it contains the neo selection marker instead of the gpt. pING4063 was constructed by ligating the ~2900 bp NotI-XhoI fragment from pING4149 (described above) with the XhoI-NotI vector fragment from pING4154 (Table I), supplying the light chain 3' sequences and the neo selection marker.

Table I, below, summarizes the content of the plasmids whose preparation is described in Sections A through H above.

TABLE I

| Plasmid | BPI Product | Signal Seq. | Marker | 3' Terminal | Promoter |
| --- | --- | --- | --- | --- | --- |
| pING4519 | (1-199)Ala$^{132}$ | 31AA | DHFR* | Human Genomic HC Gamma-1 Poly-A | A-MuLv |
| pING4520 | (1-199)Ser$^{135}$ | 31AA | DHFR* | Human Genomic HC Gamma-1 Poly-A | A-MuLv |
| pING4530 | (1-199)Ala$^{132}$ | 31AA | gpt | Human Genomic HC Gamma-1 Poly-A | A-MuLv |
| pING4533 | (1-199)Ala$^{132}$ | Kozak initiation Seq; 27AA signal | gpt | Human Genomic HC Gamma-1 Poly-A | A-MuLv |
| pING4223 | (1-193)Ala$^{132}$ | Kozak initiation Seq; 27AA signal | gpt | Human Genomic HC Gamma-1 Poly-A | A-MuLv |
| pING4221 | (1-193)Ala$^{132}$ | Kozak initiation Seq; 27AA signal | his | Human Genomic HC Gamma-1 Poly-A | A-MuLv |
| pING4222 | (1-193)Ala$^{132}$ | Kozak initiation Seq; 27AA signal | DHFR | Human Genomic HC Gamma-1 Poly-A | A-MuLv |
| pING4537 | (1-199)Ala$^{132}$ | Kozak initiation | gpt | Human Kappa Poly-A/Mouse | A-MuLv |

TABLE I-continued

| Plasmid | BPI Product | Signal Seq. | Marker | 3' Terminal | Promoter |
|---|---|---|---|---|---|
| pING4143 | (1-193)Ala$^{132}$ | Kozak initiation Seq; 27AA signal | | Human Kappa Poly-A/Mouse Kappa Genomic Transcription Termination | A-MuLv |
| pING4146 | (1-193)Ala$^{132}$ | Kozak initiation Seq; 27AA signal | DHFR | Human Kappa Poly-A/Mouse Kappa Genomic Transcription Termination | A-MuLv |
| pING4150 | (1-193)Ala$^{132}$ | Kozak initiation Seq; 27AA signal | his | Human Kappa Poly-A/Mouse Kappa Genomic Transcription Termination | A-MuLv |
| pING4144 | (1-193)Ala$^{132}$ | Kozak initiation Seq; 27AA signal | gpt | Human Kappa Poly-A/Mouse Kappa Genomic Transcription Termination | hCMV |
| pING4145 | (1-193) | Kozak initiation seq; 27AA signal | gpt | Human Kappa Poly-A/Mouse Kappa Genomic Transcription Termination | A-MuLv |
| pING4148 | (1-193) | Kozak initiation Seq; 27AA signal | DHFR | Human Kappa Poly-A/Mouse Kappa Genomic Transcription Termination | A-MuLv |
| pING4152 | (1-193) | Kozak initiation Seq; 27AA Signal | his | Human Kappa Poly-A/Mouse Kappa Genomic Transcription Termination | A-MuLv |
| pING4151 | (1-193)ala$^{132}$ | Kozak initiation Seq; 27AA signal | his | Human Kappa Poly-A/Mouse Kappa Genomic Transcription Termination | hCMV |
| pING4154 | (1-193)ala$^{132}$ | Kozak initiation Seq; 27AA signal | neo | Human Kappa Poly-A/Mouse Kappa Genomic Transcription Termination | A-MuLv |
| pING4I47 | (1-193) | Kozak initiation Seq; 27AA signal | gpt | Human Kappa Poly-A/Mouse Kappa Genomic Transcription Termination | CMV |
| pING4149 | (1-193) | Kozak initiation Seq; 27AA signal | DHFR | Human Kappa Poly-A/Mouse Kappa Genomic Transcription Termination | CMV |
| pING4153 | (1-193) | Kozak initiation Seq; 27AA signal | his | Human Kappa Poly-A/Mouse Kappa Genomic Transcription Termination | CMV |
| pING4063 | (1-193) | Kozak initiation Seq; 27AA signal | neo | Human Kappa Poly-A/Mouse Kappa Genomic Transcription Termination | CMV |

*An altered DHFR gene as described in copending, co-owned U.S. patent application, Ser. No. 07/885,911, incorporated herein by reference.

EXAMPLE 2

Stable Transfection Of Mammalian Cells For Expression of BPI Protein Products

Mammalian cells are preferred hosts for production of rBPI protein products according to the invention because such cells allow for proper secretion, folding, and post-translational modification of expressed proteins. Presently preferred mammalian host cells for production of products of the invention include cells of fibroblast and lymphoid origin, such as: CHO-K1 cells (ATCC CCL61); CHO-DG44 cells, a dihydrofolate reductase deficient [DHFR$^-$] mutant of CHO Toronto obtained from Dr. Lawrence Chasin, Columbia University; CHO-DXB-11, a DHPR$^-$ mutant of CHO-K1 obtained from Dr. Lawrence Chasin; Vero cells (ATCC CRL81); Baby Hamster Kidney (BHK) cells (ATCC CCL10); Sp2/O-Ag14 hybridoma cells (ATCC CRL1581); and NSO myeloma (ECACC No. 85110503).

Transfection of mammalian cells may be accomplished by a variety of methods. A common approach involves calcium phosphate precipitation of expression vector DNA which is subsequently taken up by host cells. Another common approach, electroporation, causes cells to take up DNA through membrane pores created by the generation of a strong electric field [(Sambrook et al., *Molecular Cloning, A Laboratory Manual*, Cold Spring Laboratory Harbor Press, 16.30–16.31 (1989)]. Selection for transfected cells is facilitated by incorporation in the expression vector of a gene whose product allows the transfected cells to survive and grow under selective conditions. A number of such genes have been identified. These include, among others: (1) the bacterial Tn5 neo gene, a prokaryotic gene which encodes resistance to the aminoglycoside antibiotic G418; (2) *E. coli* guanine phosphoribosyl transferase (gpt), which encodes resistance to mycophenolic acid (MPA) in the presence of xanthine, [Mulligan et al., *Proc. Nat. Acad. Sci. USA*, 78:2072–2076 (1981)]; (3) dihydrofolate reductase (DHFR), which allows for growth of DHFR$^-$ cells in the absence of nucleosides and gene amplification in the presence of increasing concentration of methotrexate; (4) the hisD gene of *Salmonella typhimunum* which allows growth in the presence of histidinol [Rartman et al., *Proc. Nat. Acad. Sci. USA*, 85:8047–8051, (1988)]; (5) the trpB gene of *E. coli*

[Hartman et al., *Proc. Nat. Acad. Sci. USA*, 85:8047–8051, (1988)], which allows growth in the presence of indole (without tryptophan); and (6) the glutamine synthetase gene, which allows growth in media lacking glutamine and gene amplification in the presence of methionine sulfoximine. The availability of these selective markers, either alone or in various combinations, provides flexibility in the generation of mammalian cell lines which express recombinant products at high levels.

A. Transfection Of pING4145 into CHO-K1 Cells

Plasmid pING4145 contains gene sequences encoding rBPI (1–193) fused to the A-MuLv promoter, the optimized Kozak translation initiation sequence, the mouse kappa light chain 3' untranslated sequences, along with the gpt marker for selection of MPA-resistant cells.

The CHO-K1 cell line was transfected with pING4145 DNA using the calcium phosphate method. Following transfection, the cells were allowed to recover for 24 hours in non-selective Ham's F12 medium. The cells were then trypsinized, resuspended at a concentration of about 2.5 and $5 \times 10^4$ cells/ml in Ham's F12 medium supplemented with MPA (25 μg/ml) and xanthine (250 μg/ml) and then plated at about $5 \times 10^3$ and $10^4$ cells/well in 96-well plates. Untransfected CHO-K1 cells are unable to grow in this medium due to the inhibition of pyrimidine synthesis by MPA.

At approximately 2 weeks, supernatants from 125 wells containing single colonies were analyzed for the presence of BPI-reactive protein by anti-BPI ELISA. In this assay, Immulon-II 96-well plates (Dynatech, Chantilly, Va.) were pre-coated with affinity purified rabbit anti-rBPI (1–199) antiserum. Supernatant samples were added and detection was carried out, using affinity purified, biotinylated rabbit anti-rBPI (1–199) antiserum and peroxidase labelled avidin.

The top producers were transferred to 24-well plates for productivity assessment. Cells were grown to confluence in a 24-well plate in Ham's F12 medium supplemented with 10% FBS. Once the cells reached confluence, the Ham's F12 medium was removed and 1 ml of HB-CHO serum free medium (Irvine Scientific) plus 40 μl of sterile S-sepharose beads (Pharmacia, Piscataway, N.J.) was added as in co-owned, copending U.S. patent application, Ser. No.08/072,063 by Grinna. The cells were then incubated for 7 days after which the S-sepharose beads were removed and washed with 0.1M NaCl in 10 mM Tris buffer (pH 7.5). The product was eluted from the beads by addition of 1.0M NaCl in Tris buffer and quantitated by ELISA as described above. The top-producing transformant, designated Clone C16 was chosen for re-transfection with a second plasmid, pING4063 to provide a cell line which produces optimal levels of BPI.

B. Transfection Of pING4063 into CHO-K1/pING4145/Clone C16

Plasmid pING4063 is similar to pING4145 except that it contains the human cytomegalovirus (hCMV) promoter instead of the A-MuLv promoter, and the neo gene for selection of G418-resistant cells.

The CHO-K1 Clone C16 cell line was transfected with pING4063 DNA by electroporation. Following a 48 hour recovery in Ham's F12 medium, the cells were plated in selective medium (MPA plus xanthine, as above, plus 0.6 mg/ml G418) in the manner described above in section A. At approximately two weeks, supernatants from 252 wells containing single colonies were screened for the presence of BPI-reactive protein by ELISA. The top producers were transferred to 24 well plates and BPI expression determined in 24 well plates containing S-sepharose as described above in section A. The top producer, Clone C212, was adapted to Excell 301 serum-free medium (JRH Scientific, Lenexa, Kans.), containing the selective agents as above in preparation for growth in fermenters. The adapted cells were grown in 1.5L fermenters containing Excell 301 medium supplemented with 2% fetal bovine serum. Productivity was assessed at 200–260 hours. The productivity was approximately 20–30 mg/L at this stage of the fermentation. This clone, re-designated clone C2068, was deposited with the American Type Culture Collection, 12301 Parkdawn Drive, Rockville, Md. 20852 as ATCC accession No. CRL 11535.

EXAMPLE 3

Isolation of BPI Dimer Products From Cell Culture Medium

In this example substantially pure dimeric product was isolated away from monomer products, multimer products and other materials such as nucleic acids present in the medium of transfected CHO host cells. Specifically, CHO host cells transfected with DNA encoding the secretory sequence and residues 1–199 of BPI were grown in a 750 L fermenter in the presence of a growth medium consisting of Ex-Cell 301 (J.R.H. Corporation, Lenexa, Kans.) supplemented with 0.5% fetal bovine serum, xanthine, sodium bicarbonate and 0.01% antifoam (Ucarferm™ Adjuvant 27, Union Carbide). Sterile SP-Sepharose beads were added to the fermenter. Upon termination of cell culture production in the fermenter, the suspension, consisting of cells, cell debris and SP-Sepharose beads, is dispensed into sedimentation containers. The SP-Sepharose beads were washed extensively in a series of buffers (20 mM sodium acetate/0.4M sodium chloride pH 4.0 and 20 mM sodium acetate/0.7M sodium chloride pH 4.0) and 20 mM sodium acetate/1.0M sodium chloride pH 4.0 buffer. An alternative preferred buffer to prevent cell lysis is 0.15M NaCl at pH 7.0 to remove intact cells followed by a higher NaCl concentration buffer to remove contaminants. The resulting monomer-enriched eluate of this step can be subjected to further processing as in Example 5, infra.

Elution of products remaining on the column in a single step with 1.5M NaCl-Acetate buffer provided a BPI dimer-rich (about 87%) eluate also containing BPI multimers and monomers and potentially other contaminants such as nucleic acids, proteins including histones, and the like. The eluate (2.6 liters) was diluted two-fold with water and was then loaded at 4.5 mL/minute onto a fresh 2.2×18.5 cm SP-Sepharose column which had been equilibrated with 20 mM sodium acetate, 1.0M NaCl, pH, 4.0. After loading and washing, the column was reversed and eluted with 20 mM sodium acetate, 1.5M NaCl pH 4.0. The elution peak was collected in a volume of 70 mL and had a protein concentration of 0.67 mg/mL.

The SP-Sepharose eluate was diluted 3-fold to a salt concentration of 0.5M with Milli-Q water and was then loaded at 2 mL/min onto a 1×15 cm CM-Sepharose column which had been equilibrated with 20 mM sodium acetate, 0.5M NaCl, pH 4.0. After loading and washing at 0.5M NaCl to remove monomeric BPI products, the column was reversed and eluted with 20 mM sodium acetate, 1.0M NaCl, pH 4.0 to provide a BPI protein product dimer-containing eluate. The elution peak was collected in a volume of 15 mL and had a rBPI$_{23}$ concentration of 2.05 mg/mL.

The CM-Sepharose eluate was then further purified and buffer exchanged by passing it over a 2.2×20 cm Sephacryl S-100 column that had been equilibrated with 20 mM sodium citrate, 0.15M NaCl, pH 5.0. The flow rate was 1.5 mL/minute and the product pool was collected in a volume of 35 mL.

The concentration of dimer at this stage was 1.15 mg/mL. Excipients were added and the sample was diluted to give a final product at 1 mg/mL in 20 mM sodium citrate, 0.15 M NaCl, pH 5.0 with 0.1% poloxamer 188 and 0.002% polysorbate 80. This material was sterile filtered using a Millex GV 0.22 m filter into sterile 10 mL Hollister-Stier vials. Analysis of the final product indicated that it contained 40 mg dimer (50% yield) that was >99% pure. This is compared with the 1.5M NaCl-Acetate dimer-rich eluate from the first SP-Sepharose column which had a desired protein concentration of 18 µg/mL, 87% of which was dimer. DNA was removed throughout the various steps of the process but a significant proportion of the DNA was removed during elution from the SP-Sepharose and CM-Sepharose columns where DNA was dissociated from the BPI protein products at pH 4.0. Analysis of the dimeric product revealed that it predominantly included monomers having BPI residues 1–199.

EXAMPLE 4

Comparison of Metal Ions As Dimer Formation Catalysts

Various metal ions ($Cu^{2+}$, $Ca^{2+}$, $Zn^{2+}$, $Mg^{2+}$ and $Mn^{2+}$) were evaluated to determine if they would promote the formation of BPI dimer. Specifically, 2 µL of ten-fold dilutions (1 mM, 0.1 mM and 0.01 mM) of $CuSO_4$, $ZnCl_2$, $CaCl_2$, $MgCl_2$, and $MnCl_2$, were added into 18 µL of $rBPI_{23}$ adjusted to pH 7.0 with 0.5 M Tris, pH 10.6 and incubated for one hour at 37° C. A 1 µg aliquot of each sample was then run on a 12.5% non-reduced SDS gel to determine the presence of dimer. The results showed dimer formation for the 1 mM and 0.1 mM $Cu^{2+}$ samples but did not show dimer formation for the 0.01 mM $Cu^{2+}$ or for the samples containing the other ions.

The experiment was repeated for ten-fold lower concentration (100 µM, 10 µM and 1 µM) samples for each of the ions and the samples were incubated for 24 hours instead of 1 hour. The results indicated dimer formation only for the 100 µM $CuSO_4$ sample which was the lowest concentration giving a positive result in the earlier example. This result suggests that the majority of dimer formation occurred in the first hour.

EXAMPLE 5

Conversion To Form Dimer

According to this example, a BPI protein product is converted to dimer by reaction in the presence of cupric sulfate ($CuSO_4$). A purified, formulated $rBPI_{23}$ product solution comprising 1 mg/mL $rBPI_{23}$ generally isolated by practice of Steps A through C of Example 6, infra (and containing from 2 to 8 percent by weight dimeric product) in the presence of 20 mM citrate pH 5.0, 150 mM NaCl, 0.1% poloxamer 188, and 0.002% polysorbate 80 was exchanged into 50 mM Tris-HCl, 150 mM NaCl, pH 8.0 by gel filtration using a Sephadex G-25 column. The BPI solution was then concentrated to about 1 mg/mL and sterile filtered with Millipore Millex GV 0.22 µM filters. $CuSO_4$ was added to various concentrations using either a 0.1 mM or a 1 mM stock solution. Samples were taken at defined intervals and the dimer conversion reaction was quenched after 22 hours by running the samples over a Sephadex G-25 column equilibrated in 20 mM citrate at pH 3.5 to remove the copper sulfate and reduce the reaction pH. The samples were then analyzed by ion exchange (MA7C) HPLC to determine the relative proportions of monomer and dimer.

Figure 2:
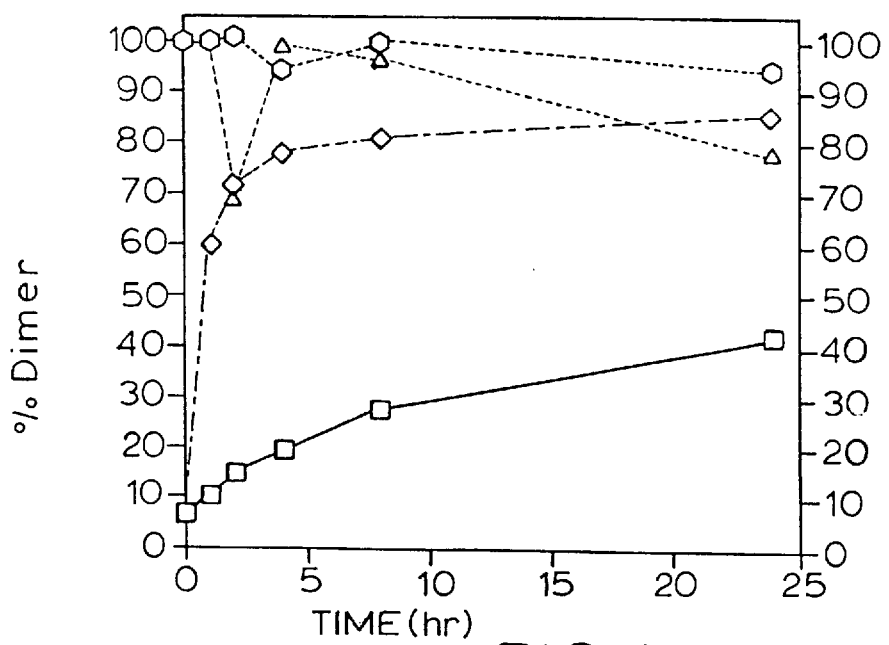
FIG. 2 depicts the conversion of BPI monomer to BPI dimer versus time.

The results (FIG. 1) illustrate that the percent dimer formed from monomer increases as a function of cupric sulfate concentration at pH 8.0 but that at $CuSO_4$ concentrations above 5 µM little additional dimer was formed at 22 hours. Results from other experiments indicate that the rate of interchain disulfide formation is also a function of BPI concentration. FIG. 2 depicts the results of a 24-hour time course of forming BPI dimer from the $rBPI_{23}$ monomer (1.0 mg/mL), at room temperature and either pH 7.0 or 8.0. The data is depicted as follows: —□—,% Dimer pH 7.0; . . . ◊ . . . ,% Dimer pH 8.0; . . . ○ . . . , % Recovery pH 7.0; and . . . ∆ . . . , % Recovery pH 8.0. The results show that dimer formation proceeds more slowly at pH 7.0 (42% conversion after 24 hours) than at pH 8.0 (85% conversion). The slower formation at pH 7.0 may be due to a lower concentration of cupric sulfate as a result of copper precipitation in the presence of phosphate buffer. Nevertheless, the recovery of BPI dimer is higher at pH 7.0 than at pH 8.0. This agrees with observations that BPI monomers and dimers are less stable or soluble at higher pH values. Results from other experiments indicated that the rate of dimer formation is greater at room temperature than at 4° C. while product recovery is greater at 4° C. than at room temperature. A comparison of the rates of dimer formation and protein recovery using Tris as opposed to phosphate buffers indicated little difference between the two.

The presence of $CuSO_4$ at 10 µM can accelerate the formation of dimer from monomer at pH 8 to greater than 85% in 5 hours if the starting material is first reduced with DTT to eliminate cysteine adducts. Without reduction, greater than 75% of the monomer can be converted in 5 hours.

EXAMPLE 6

Purification And Conversion To Form Dimer

A. Initial Isolation of Monomer

In this example, an alternative method for isolation of dimeric materials from heterogeneous recombinant BPI protein product preparations is presented. Specifically, transfected CHO cells expressing rBPI (1–193) were grown in the presence of SP-Sepharose beads. Growth medium and SP-Sepharose resin were removed from roller bottles, pooled and left for at least 15 minutes to allow the SP-Sepharose to settle to the bottom of the container. The bulk of the medium, clear of resin, was removed by decanting and then filtered through a device, such as a fritted disc, to permit the removal of cells and the retention of the SP-Sepharose. Following the decanting of the medium, the SP-Sepharose was washed with 20 mM sodium acetate, pH 4.0, 0.4M sodium chloride and washed again with 20 mM sodium acetate, pH 4.0, 0.65M sodium chloride. An alternative preferred buffer to prevent cell lysis is 0.15M NaCl at pH 7.0 to remove intact cells followed by a higher NaCl concentration buffer to remove contaminants. The SP-Sepharose was then eluted in a buffer comprising 20 mM sodium acetate/acetic acid at pH 4.0 containing 1.0M NaCl, and 5 mM glycine at a flow rate of 100 cm/hour. The eluate was primarily monomeric BPI and the BPI which remained on the column was primarily dimeric BPI.

B. Optional Virus Inactivation

The eluate was then subjected to an optional virus inactivation step comprising adjusting the eluate to pH 3.0+/−0.1 with 10% hydrochloric acid and allowing it to stand at 2°–8° C. for approximately two hours. The pH was then adjusted to 4.0+/−0.1 with 1N sodium hydroxide and diluted with water to 0.25M sodium chloride.

C. Concentration

The primarily monomeric BPI protein product preparation was then subjected to a purification and concentration step wherein it was loaded onto a 1.6×10.0 cm CM-Sepharose column having a capacity of about 20 mL CM-Sepharose which had been pre-equilibrated with 20 mM sodium acetate, pH 4.0, 0.25 sodium chloride. The CM-Sepharose had a binding capacity of 15 mg/mL BPI and the column was capable of a flow rate of 750 cm/hour. The column was washed with 30 column volumes of 20 mM sodium acetate, pH 4.0, 0.35M sodium chloride and the BPI monomer was eluted with 20 mM sodium acetate, pH 8.7, 20 mM Tris, 0.6M sodium chloride.

D. Dimerization and Recovery

The BPI preparation was filter sterilized and adjusted to pH 8.0 with 1M sodium hydroxide and a 1 mM stock solution of copper sulfate was added to bring the $CuSO_4$ concentration to 10 $\mu$M. The preparation was then incubated for 16–20 hours at room temperature to effect conversion to dimer. Alternatively, $CuSO_4$ could be added to a concentration of 30 $\mu$M in a 20 mM sodium acetate, 20 mM Tris, 0.6M NaCl solution at pH 8.0 and the preparation incubated at 4° C. overnight. As a further alternative, the preparation could be incubated with 30 $\mu$M $CuSO_4$ and 1M NaCl, 20 mM acetate at pH 5.0. After dimerization, the dimer/monomer ratio was approximately 3:1 by weight.

The pH of the resulting dimer-containing preparation was adjusted to 5.0 with 10% HCl and two volumes of water and the solution was applied to a 1×3 cm CM-Spherodex column having a volume of about 2.5 mL which had been equilibrated with 20 mM sodium acetate, pH 5.0, 0.2 sodium chloride. The CM-Spherodex had a binding capacity of 30 mg/mL BPI and the column was capable of a flow rate of 300 cm/hour. The column was washed with 10 column volumes of 20 mM sodium acetate, 0.5M sodium chloride pH 5.0 to remove nonconverted monomer, and BPI dimer was then eluted with 20 mM sodium citrate, 1.0M sodium chloride, pH 5.0. The CM-Sepharose and CM-Spherodex filtrations are believed to remove significant levels of DNA and other impurities in the preparation. For example, DNA was removed during elution from the CM-Sepharose columns when DNA was dissociated from the BPI protein products at pH 4.0.

The CM-Spherodex dimer-containing eluate was applied to a 4.4×100 cm Sephacryl S-100 column equilibrated with equilibration buffer (5 mM sodium citrate, 0.15M sodium chloride pH 5.0) and the column was developed with the equilibration buffer at about 6 mL/minute (21.6 cm/hour). The resulting BPI product was greater than 95% dimer by weight.

EXAMPLE 7

Effects in A Rat Endotoxemia Model

In this example, a rat LPS infusion experimental endotoxemia model was used to evaluate the effects of formulations of $rBPI_{23}$, $rBPI_{21}\Delta cys$, and BPI dimer on serum TNF levels. Groups of 4–10 rats were anesthetized and were subjected to intravenous infusion into the jugular vein with E. coli 0111:B4 endotoxin at a dosage of 0.25 mg/kg over a 30 minute period. Each rat was simultaneously infused into the femoral vein with various concentrations of test compound or the buffer vehicle as a control. The animals were then bled from the femoral vein at various times for a TNF determination using a standard assay with the results shown in FIG. 3. The data is depicted as follows: —□—, vehicle; - - - ▲ - - -, $rBPI_{21}\Delta cys$ (3 mg/kg); —Δ—, BPI dimer (0.1 mg/kg); —●—, $rBPI_{23}$ (0.3 mg/kg); - - - Δ - - -, $rBPI_{21}\Delta cys$ (10 mg/kg); —○—, rBPI23 (3 mg/kg); - - - ♦ - - -, $rBPI_{21}\Delta cys$ (20 mg/kg); —■— BPI dimer (1 mg/kg). Specifically, BPI dimer (0.1 mg/kg), $rBPI_{23}$ (0.3 mg/kg), $rBPI_2\Delta cys$ (10 mg/kg), $rBPI_{23}$ (3 mg/kg) and $rBPI_2\Delta cys$ (20 mg/kg) were all significantly different from vehicle and $rBPI_21\Delta cys$ (3 mg/kg) but not significantly different from each other. Effects of BPI dimer (1 mg/kg) were significantly different from all groups except for $rBPI_2\Delta cys$ (20 mg/kg). As observed with other endotoxemia models TNFA levels peaked 90 minutes after endotoxin infusion began and then returned toward control levels. Dosages of 0.3 to 3.0 mg/kg of $rBPI_{23}$ resulted in approximately a 60% reduction in TNF levels compared to the buffer treated animals. Dosages of 10–20 mg/kg $rBPI_2\Delta cys$ were required to reduce TNF levels to the same degree as $rBPI_{23}$ (3.0 mg/kg). In contrast, a dosage of BPI dimer at 0.1 mg/kg significantly inhibited TNF release. This level of inhibition was comparable to that achieved with 0.3 mg/kg of $rBPI_{23}$ or 10 mg/kg of $rBPI_{21}\Delta cys$.

The observed enhanced in vivo biological activities of formulations including dimeric BPI protein product forms were particularly unexpected in view of in vitro assays wherein activities of products with high concentrations of dimeric molecular forms were not significantly different from those with lesser concentrations. Specifically, in an ex vivo cytokine assay for TNF production where E. coli O113 LPS was incubated in the presence of human peripheral blood BPI dimer inhibited TNF production with similar potency to that of monomer when compared on a molar basis. In a broth dilution antibacterial assay BPI dimer and monomer were equally potent on a molar basis against E. coli J5. In a radial diffusion assay against E. coli J5 BPI dimer appeared to be less active than monomer. The lower antibacterial activity of dimer in the radial diffusion assay may be an artifact due to the lower diffusion of dimer through the agarose because a Coomassie Blue-stained halo was observed around the wells for the dimer but not the monomer.

EXAMPLE 8

Effect Of Dimer In A Rabbit Endotoxemia Model

In this example, a conscious rabbit endotoxemia model was used to evaluate the effects of various BPI protein products on cardiopulmonary function. These BPI protein products included $rBPI_{23}$, $rBPI_2\Delta cys$ and BPI dimer.

Rabbits under anesthesia were instrumented for measurement of blood pressure, heart rate, and cardiac output. After recovery from anesthesia 6 $\mu$g/kg of E. coli 0113 endotoxin was injected into a marginal ear vein over a 60 second period. Test products at dosages of from 0.5–4 mg/kg were injected into a jugular vein over a 120 second period beginning 30 seconds before administration of endotoxin. Cardiovascular and respiratory parameters were then measured for a 3 hour period and blood samples were obtained periodically in order to measure blood gases.

Figure 4:
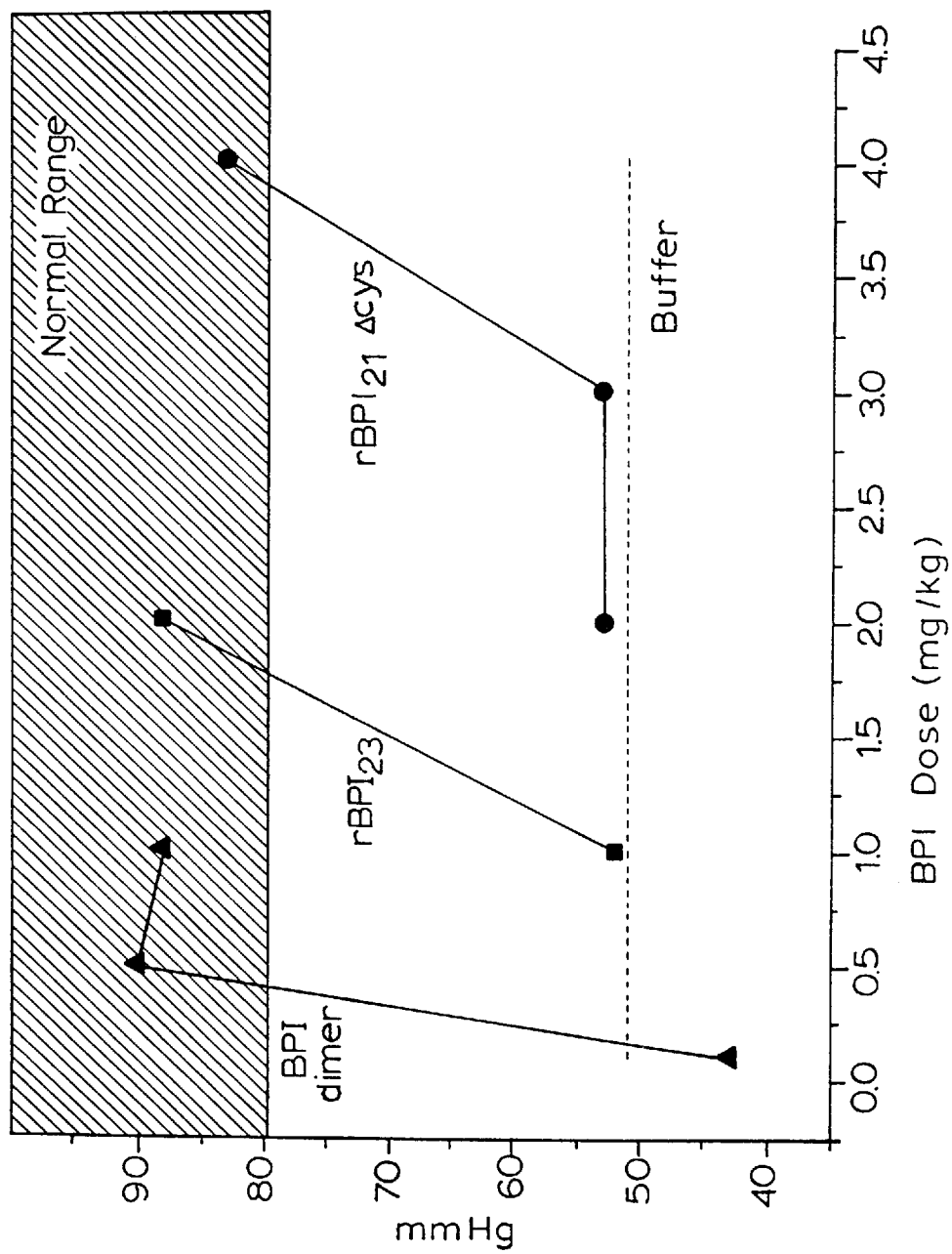
FIG. 4 depicts the effects of BPI protein products on mean arterial blood pressure in a rabbit endotoxemia model.

The results illustrated in FIG. 4 disclose the effect of the BPI proteins compared with a buffer control on mean arterial blood pressure in the rabbit endotoxemia model. Blood pressure of the animals decreased after endotoxin challenge and reached levels close to 50 mmHg by 60 minutes into the experiment. It required 4 mg/kg $rBPI_{21}\Delta cys$ to prevent the decrease in blood pressure and to maintain pressure in the normal range of about 80–100 mmHg throughout the experiment. A dosage of 2 mg/kg of $rBPI_{23}$ was sufficient to prevent decreases in blood pressure outside of the normal range throughout the experiment. In contrast, a dosage of only 0.5 mg/kg of the dimer was required to prevent decreases in blood pressure outside of the normal range throughout the experiment.

Figure 5:
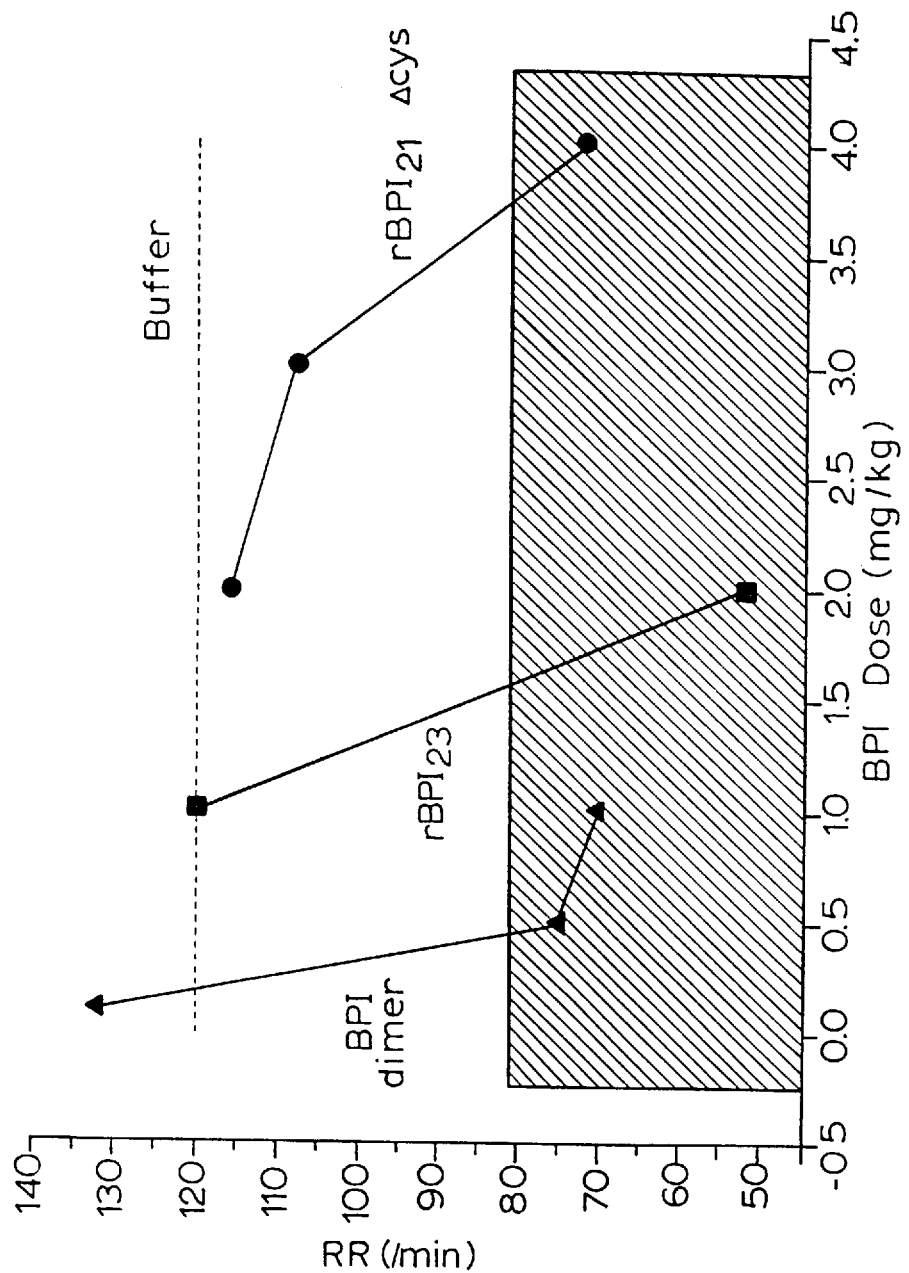
FIG. 5 depicts the effects of BPI protein products on respiratory rate in a rabbit endotoxemia model.

Evaluation of changes in cardiac index indicated that the cardiac index was significantly reduced in animals treated only with the buffer control. The decrease in cardiac index was reduced or eliminated with treatment of BPI proteins. Specifically a dosage of 4 mg/kg of rBPI$_2$Δcys, 2 mg/kg rBPI$_{23}$, and 0.5 mg/kg BPI dimer neutralized the effect of endotoxemia on cardiac output. Similar neutraliztion effects were observed with respect to decreases in total peripheral resistance, with respect to elevated heart rate, and with respect to elevated respiratory rate (see FIG. 5).

EXAMPLE 9

Comparative Activity Of Reduced Monomeric) rBPI$_{23}$ In a Rat Endotoxemia Model In this example, the activity of an rBPI$_{23}$ preparation substantially free of dimer was determined in a rat experimental endotoxemia model. In this manner, the overall contribution to biological activity (such as observed in Example 8) of BPI dimer component present in fermenter produced rBPI$_{23}$ could be determined. Specifically, the monomeric preparation was produced by treatment of fermenter produced rBPI$_{23}$ with 20 mM dithiothreitol (DTT) at pH 7.0 for 30 minutes at room temperature. A study using the rat LPS infusion model according to Example 7 was then conducted to determine the activity of the product. Groups of five rats each were simultaneously infused (30 minutes, i.v.) with 0111 :B4 LPS (0.25 mg/kg) and either DTT-reduced rBPI$_{23}$ (0.3, 3.0 or 10.0 mg/kg), rBPI$_{21}$Δcys (3.0 or 10.0 mg/kg) or vehicle. The reducing agent was present in all preparations.

Figure 6:
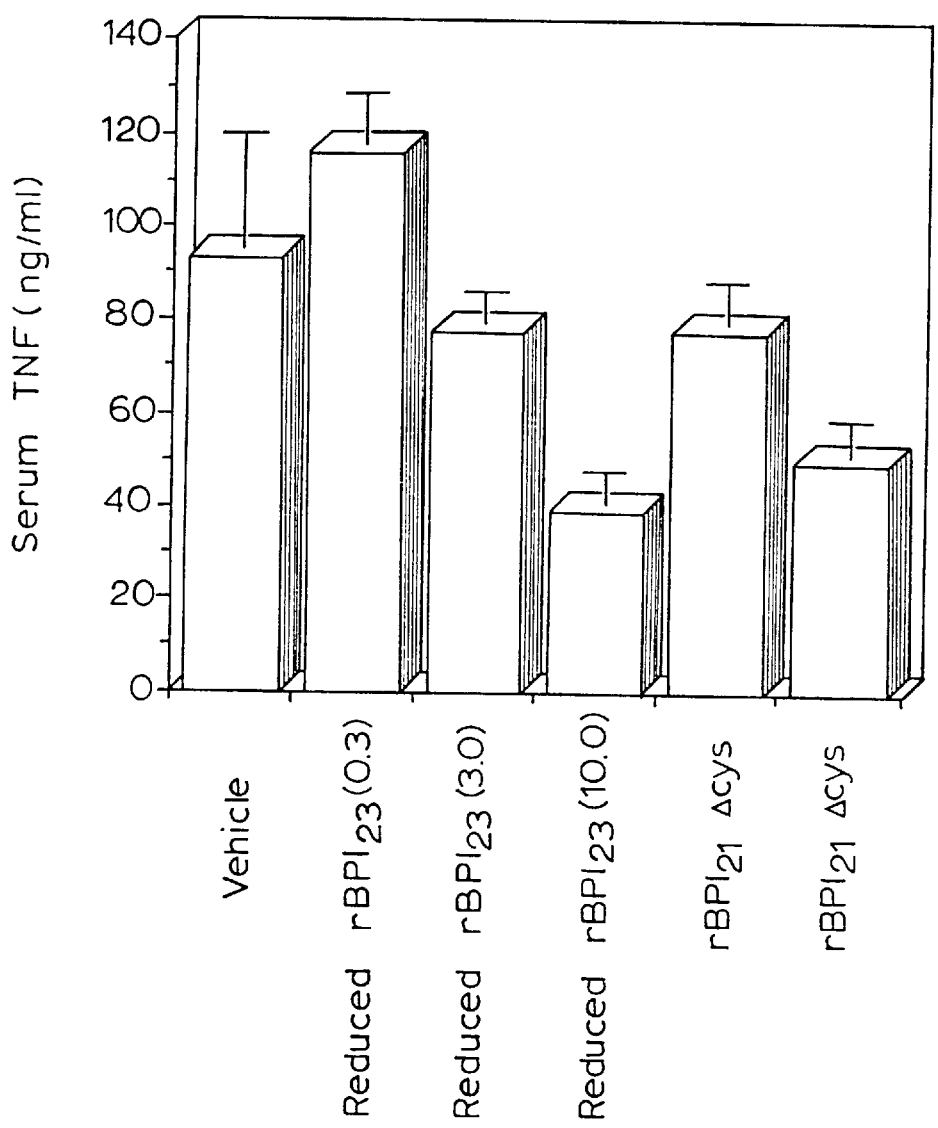
FIG. 6 depicts the effects of BPI protein products on TNF levels in a rat LPS infusion endotoxemia model.

Serum was collected at 90 minutes and assayed for TNF with the mean value results shown in FIG. 6. None of the BPI-treated groups had TNF levels that were statistically significantly lower than the vehicle control group. This was due to the considerable variability in the control group in this study and the small number of animals per group. Nevertheless, there was a trend toward inhibition of TNF release at a 10 mg/kg dose of rBPI$_2$Δcys. The magnitude of the inhibition was similar to that obtained with this dose in Example 7. There was also a trend toward inhibition with the 10 mg/kg dose of the monomeric preparation. Therefore, the monomeric preparation appeared to have a similar potency to the rBPI$_{21}$Δcys. Moreover, the monomeric preparation apparently has a lower potency than non-reduced rBPI$_{23}$ which has been shown to be effective at a dose as low as 0.3 mg/kg (e.g., Example 7). These results suggest that the presence of BPI dimer in preparations of rBPI$_{23}$ may account for its increased potency relative to rBPI$_{21}$Δcys.

EXAMPLE 10

Effect Of Dimer In A Mouse Peritonitis Model

Figure 7:
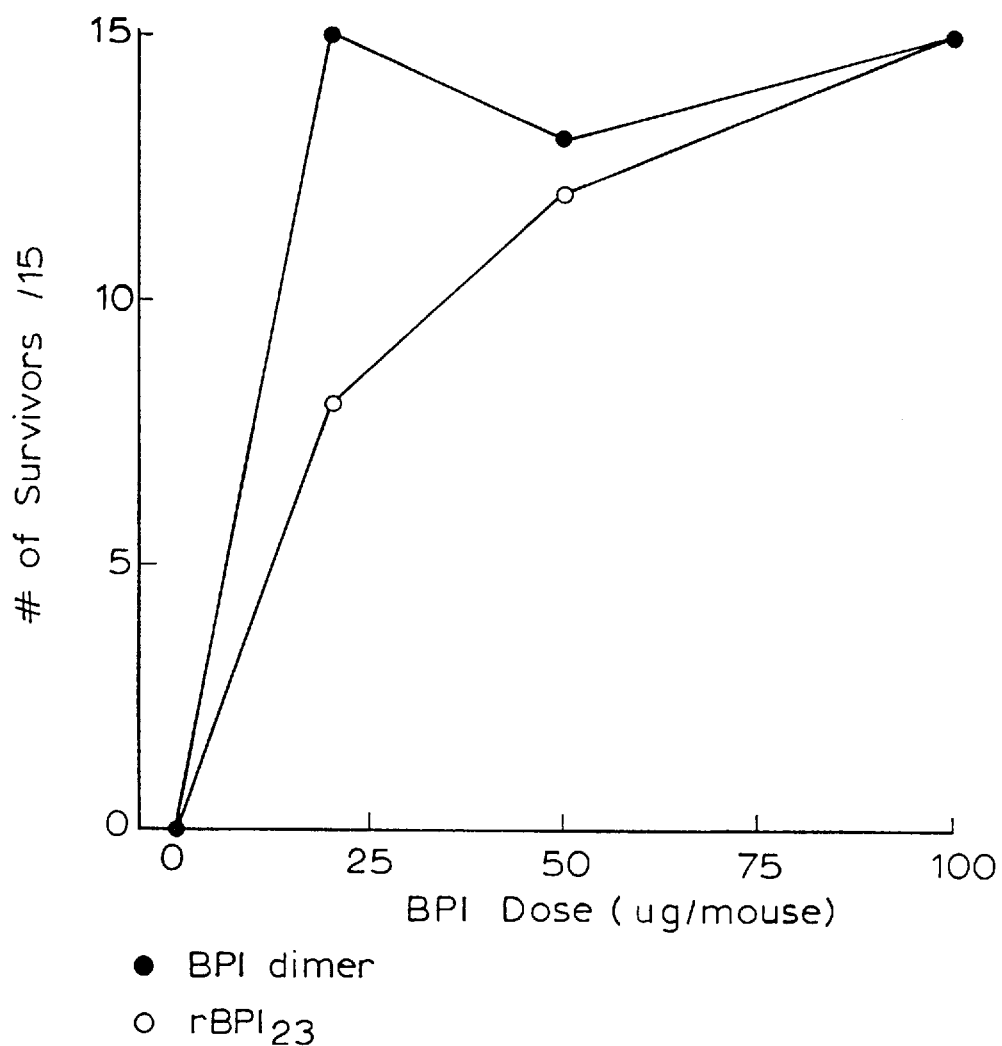
FIG. 7 depicts the results of BPI administration in a mouse acute peritonitis model.

In this example, the efficacy of BPI dimer and fermenter produced rBPI$_{23}$ was determined in a mouse model of acute peritonitis. Groups of 15 mice were challenged with 10$^7$ live E. coli bacteria (strain 07:K1) in 0.5 mL volumes and then treated with 20, 50, or 100 μg of dimer, or rBPI$_{23}$ in 1 mL volumes or an equal volume of buffer. The animals were observed for 7 days and mortality recorded. FIG. 7 shows the final number of survivors at each dose with the 0 dose representing the mice given buffer. While the effects of the high doses of the constructs were not significantly different, the 20 μg dose of BPI dimer was significantly more protective than the same dose of rBPI$_{23}$.

EXAMPLE 11

Effects in a Mouse Endotoxemia Model

In this example, BPI dimer was tested for its efficacy in a mouse experimental endotoxemia model. Groups of 15 mice were administered an intravenous injection of endotoxin (E. coli O111:B4, Sigma Chemical Co., St. Louis, Mo.) at a LD$_{90}$ dosage of 40 mg/kg. This was followed by a second intravenous injection of the BPI dimer or rBPI$_{21}$Δcys. Injections of buffer were used in negative control mice. The animals were observed for 7 days and mortality recorded. A 10 mg/kg dose of BPI dimer was effective to protect all treated animals (100% survival). A 30 mg/kg dose of rBPI$_{21}$Δcys was required to similarly protect the treated mice. No animals survived in the buffer control group.

EXAMPLE 12

Pharmacokinetics Of BPI Dimer In Rats

Figure 14:
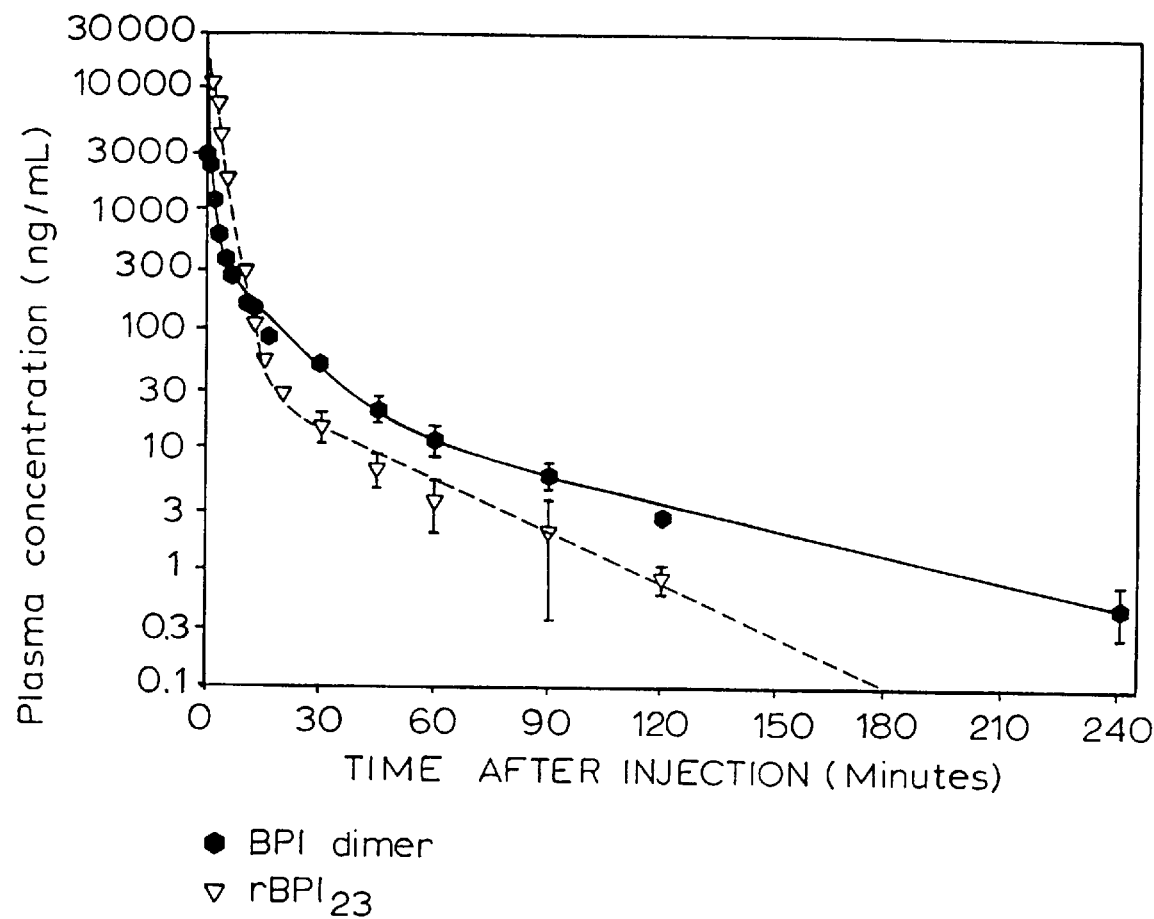
FIG. 14 graphically depicts pharmacokinetic properties.

In this example, the pharmacokinetics of BPI dimer in rats was compared with that of fermenter produced rBPI$_{23}$. Rats were given intravenous bolus injections with 1 mg/kg of either fermenter produced rBPI$_{23}$ or BPI dimer. BPI levels were then determined in plasma samples taken from the rats at various time points by ELISA assay. The results shown in FIG. 14 depict that rBPI$_{23}$ and BPI dimer both cleared rapidly from the plasma with systemic mean residence times of 1–3 minutes, but their distribution patterns differed considerably: the steady state volume of distribution for BPI dimer was in the range of about 700–1100 mL/kg versus 70–120 mL/kg for rBPI$_{23}$.

Western blot analysis conducted of serum of rats into which BPI dimer had been injected found no detectable monomer indicating that there is negligible break down of BPI dimer in vivo.

EXAMPLE 13

Binding of LPS to BPI Protein Products Pre-Bound To Human Endothelial Cells

In this example, rBPI$_{23}$, rBPI$_2$Δcys, and BPI dimer were compared with regard to their abilities to bind LPS after the BPI protein products were prebound to human endothelial cells. A "sandwich experiment" was performed in which confluent human umbilical vein endothelial cells EEC) were first incubated with various BPI protein products, the cultures washed, and then incubated with labelled LPS molecules.

Figure 8:
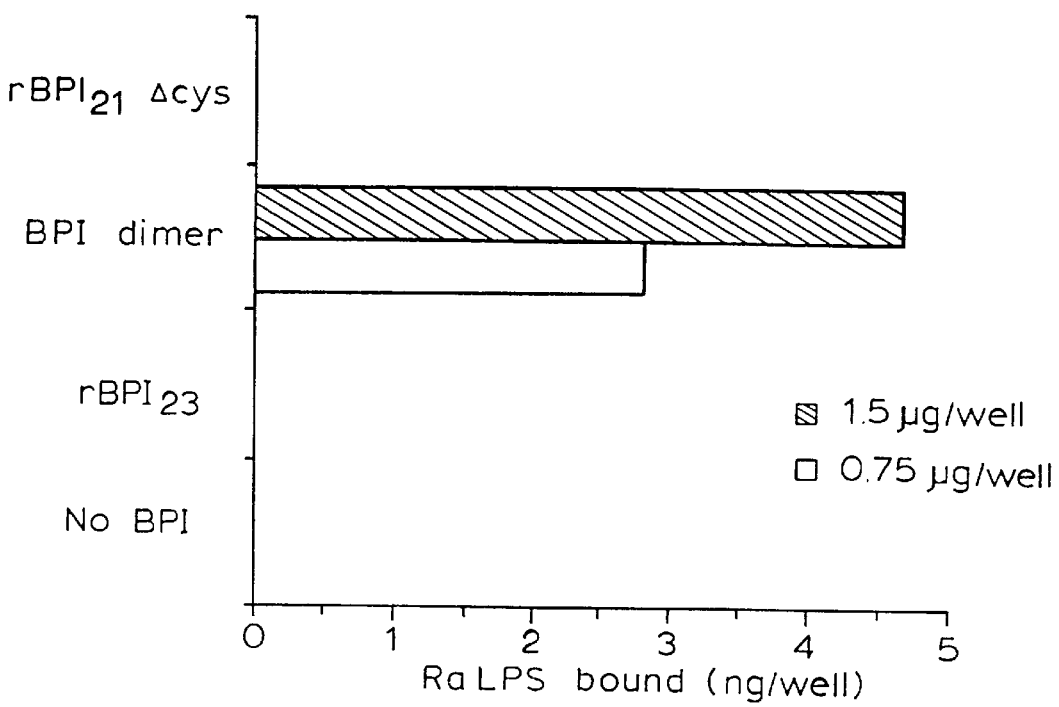
FIG. 8 graphically depicts the ability of BPI protein products to bind $^{125}$I-LPS while bound to HUVEC cells.

Specifically, HUVEC cells were obtained from Clonetics (San Diego, Calif.) and cultured for 5 to 12 passages in Endothelial Cell Growth Medium (EGM-UV) purchased from Clonetics. The HUTVEC cells were grown in 24-well microtiter plates (seeding density=5×10$^4$ cells/well) in EGM-UV, for 3 days in order to get confluent monolayers. The HUVEC cells were washed twice in PBS/0.1% BSA (PBS/BSA) and incubated in the presence of 0.75 μg or 1.5 μg of the test products for 3 hours at 4° C. in 500 μl PBS/BSA. Following incubation, the cells were washed twice with cold PBS/BSA and incubated with 500 μL PBS/BSA containing $^{125}$I-RaLPS (231,000 cpm=50 μg/well) with or without 1000-fold excess unlabeled RaLPS (50 μg/well) for an additional 2.5 hours at 4° C. The cells were then washed 3 times with PBS/BSA, solubilized with 500 μl of 1M sodium hydroxide and the lysates counted in a gamma counter. The binding of $^{125}$-RaLPS in the presence of 1000 fold excess unlabeled RaLPS was taken to represent non-specific binding with specific binding of $^{125}$I-RALPS defined as the difference between total and non-specific binding. The results are shown in FIG. 8 with the amount of RaLPS bound expressed as ng/well. Those results indicate that only dimer retained the ability to bind $^{125}$I-LPS when it was bound to HUVEC cells while rBPI$_{23}$ and rBPI$_{21}$Δcys did not.

Figure 9:
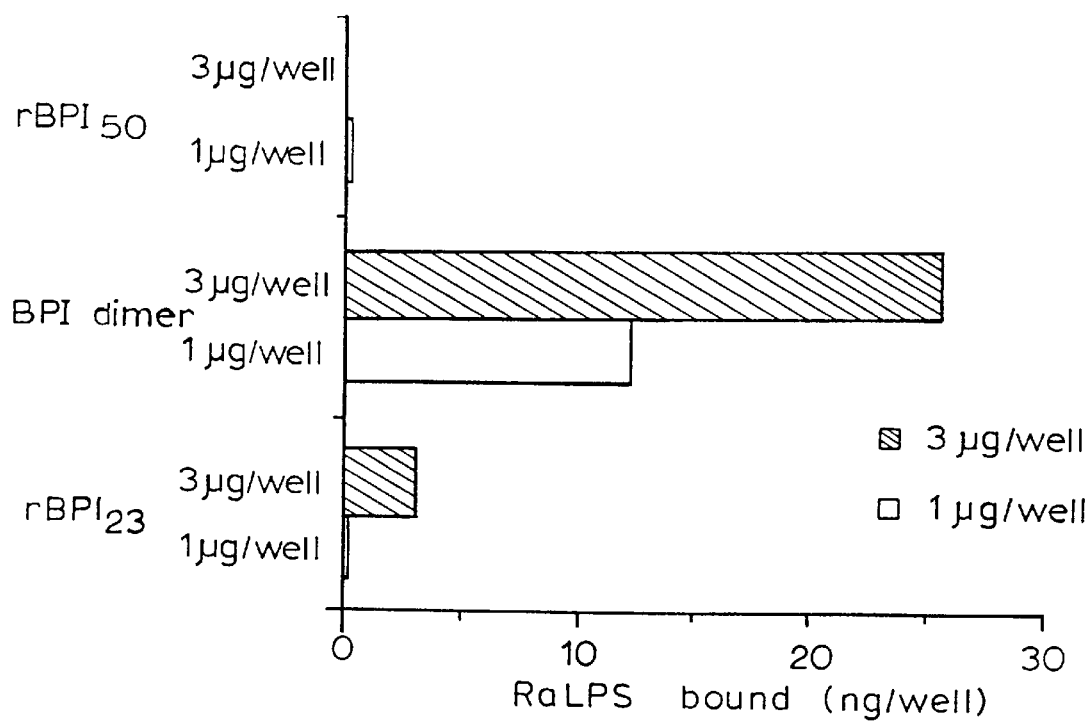
FIG. 9 graphically depicts the ability of BPI protein products to bind $^{125}$I-LPS while bound to HUVEC cells.

The procedure described above was essentially reproduced with the exception that the HUTVEC cells were incubated in the presence of 1 μg or 3 μg of the various BPI protein products (including rBPI$_{23}$, recombinant BPI holoprotein and BPI dimer) for 3 hours at 4° C. in 500 μl PBS/BSA containing 125I-RaLPS (340,000 cpm=73 ng/well) for an additional 2.5 hours at 4° C. The cells were then washed 3 times with PBS/BSA, solubilized with 500 μl of 1M sodium hydroxide and the lysates counted in a gamma counter. The results in FIG. 9 show high levels of binding by the BPI dimer. Consistent with the results of the earlier procedure, there was no significant binding of $^{125}$I-LPS by rBPI$_{23}$ at a concentration of 1 μg/well, but there was some binding at a concentration of 3 μg/well. This may be a consequence of the presence of low levels of dimer in the rBPI$_{23}$ preparation. The rBPI holoprotein failed to bind $^{125}$I-LPS to any significant extent. Further experimentation indicated that BPI dimer is bound to HUVEC cells to about the same degree as fermenter produced rBPI$_{23}$ and rBPI$_{21}$Δcys. This suggests that the dramatically enhanced ability of BPI dimer to bind to LPS in these assays is not due to the greater binding of dimer to the cells. Still further experimentation established that dimer which is bound to HUVEC cells at physiological temperatures (37° C. rather than 4° C.) retains its ability to bind $^{124}$I-RaLPS.

EXAMPLE 14

Figure 10:
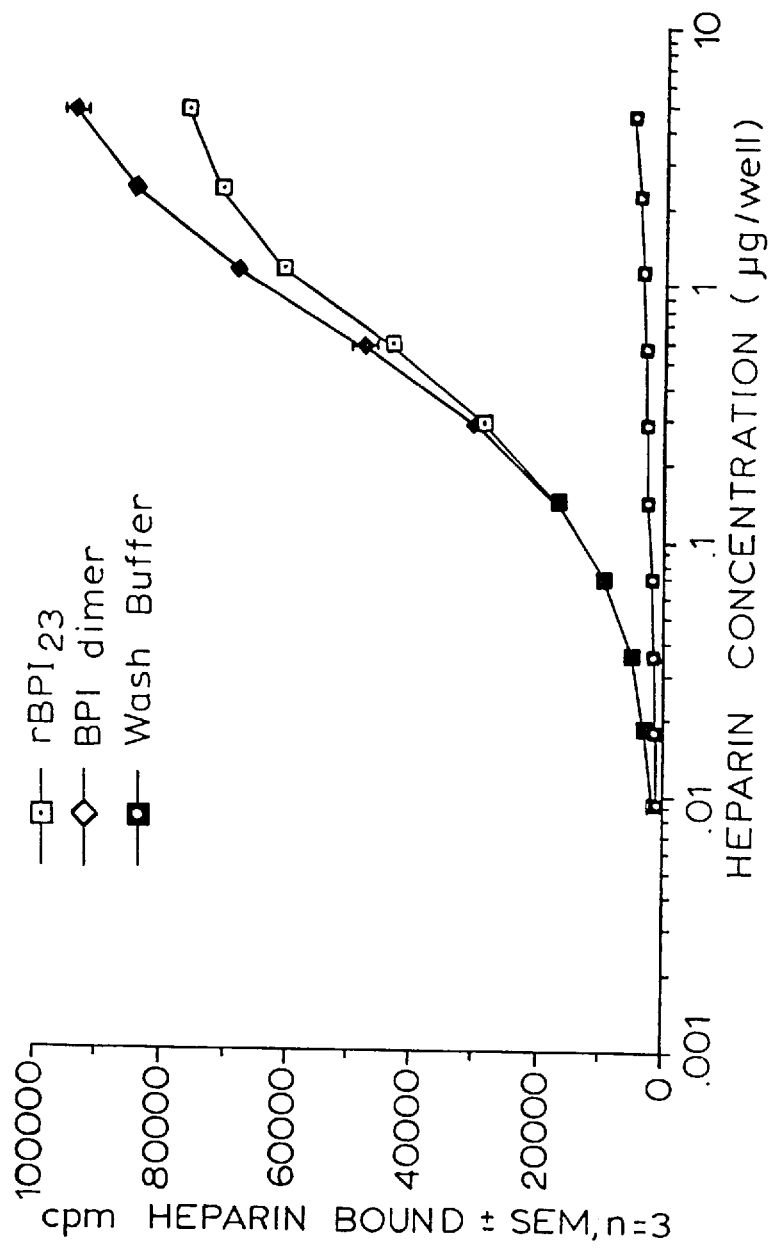
FIG. 10 graphically depicts the results of a heparin binding assay for rBPI$_{23}$ and rBPI$_{23}$ dimer.

Heparin Binding By BPI Protein Products:

The capacity of BPI protein products including BPI dimer to bind to heparin was determined using membrane bound natural and recombinant BPI molecules and radiolabelled heparin. Briefly, rBPI23 and BPI dimer were added to wells of a 96-well microtiter plate having an Immobilon-P (Millipore, Bedford, Me.) membrane disposed at the bottom of the wells. Two μg of protein was added to each well. The wells were dried and subsequently blocked with a 0.1% bovine serum albumin (BSA) in phosphate buffered saline, pH 7.4 (blocking buffer.) Dilutions of $^3$H-heparin (DuPont, NEN, Wilmington, Del.) were made in the blocking buffer and incubated in the BPI containing wells for one hour at 4° C. The unbound heparin is aspirated and the wells were washed three times with blocking buffer, dried and removed for quantitation in a liquid scintillation counter. Typical assay results are graphically presented in FIG. 10. These results show that BPI dimer has significantly greater heparin binding than does the monomer. While BSA in the blocking buffer does have a low affinity and capacity to bind heparin, this was considered physiologically irrelevant and the background was routinely subtracted from the test compound signal.

In addition, binding constants with $^3$H-heparin as the ligand were determined using nonlinear function minimization with Grafit software (Erithicus Softward Ltd., Staines, UK) for rBPI$_{23}$, and BPI dimer with the results shown in Table 2 below.

TABLE 2

| Binding Constants with $^3$H-heparin as the Ligand | | |
|---|---|---|
| PROTEIN | K$_d$ | CAPACITY |
| rBPI$_{23}$ | 274 nM +/−0.44 | 244 ng +/−3.7 |
| BPI Dimer | 345 nM +/−0.42 | 293.3 ng +/−3.3 |

EXAMPLE 15

Figure 11:
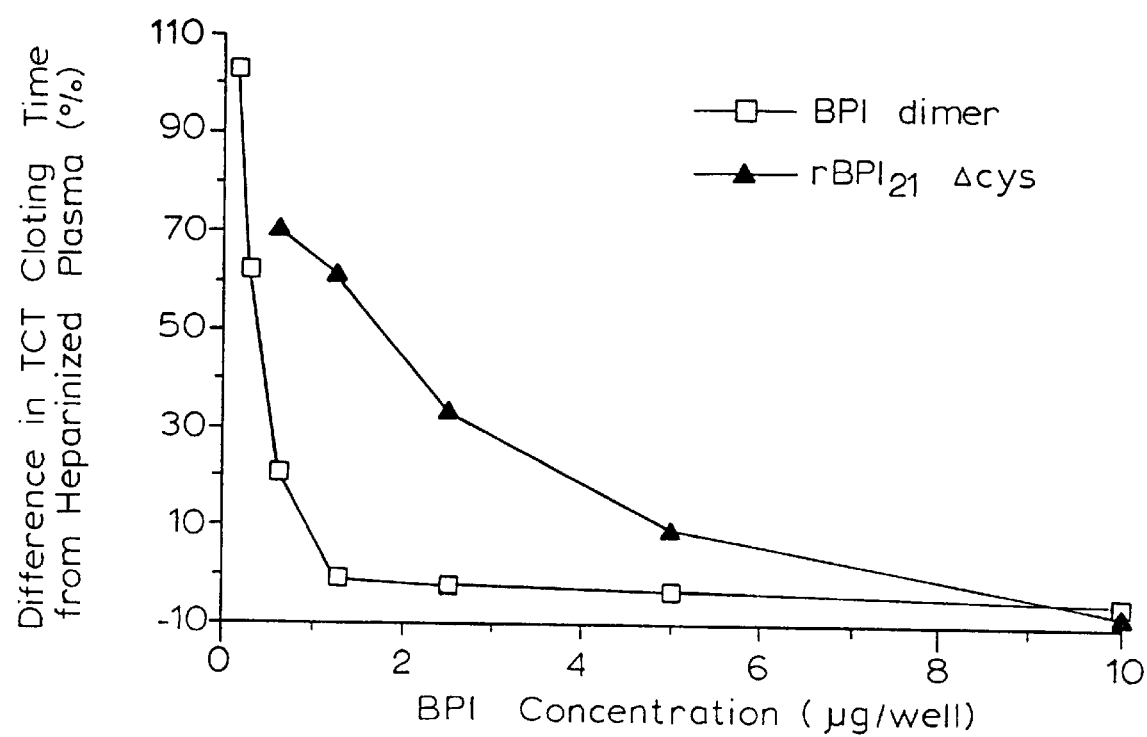
FIG. 11 graphically depicts the effects of rBPI$_{23}$ dimer and rBPI$_2$Δcys on heparin mediated lengthening of thrombin time in vitro.

Heparin Neutralization By BPI Protein Products: Effect Of BPI Dimer On Heparin-Mediated Lengthening Of Thrombin Time In Vitro The effect of BPI protein products on heparin-mediated lengthening of thrombin time, i.e., the time required for clotting of a mixture of thrombin and plasma was examined. Thrombin time is lengthened by the presence of endogenous or exogenous inhibitors of thrombin formation, such as therapeutically administered heparin. Agents which neutralize the anti-coagulant effects of heparin will reduce the thrombin time measured by the test. Human citrated plasma (200 μL) was incubated for 1 minute at 37° C. with either 15 μL of diluent (0.15M NaCl, 0.1M Tris, pH 7.4) or 15 μL of the diluent also containing 25 μg/mL heparin (187 units/mg). Various concentrations of BPI dimer and rBPI$_{21}$Δcys in volumes of 15 μL were added, followed immediately by 100 μL of thrombin reagent (Sigma Chemical Co., No. 845-4). Clotting time (thrombin time) was measured using a BBL Fibrometer Becton Dickenson Microbiology Systems, Cockeysville, Md.). The results shown in FIG. 11 establish that both BPI protein products inhibit the heparin-mediated lengthening of thrombin time but that the BPI dimer does so at significantly lower weight concentrations.

EXAMPLE 16

Figure 12:
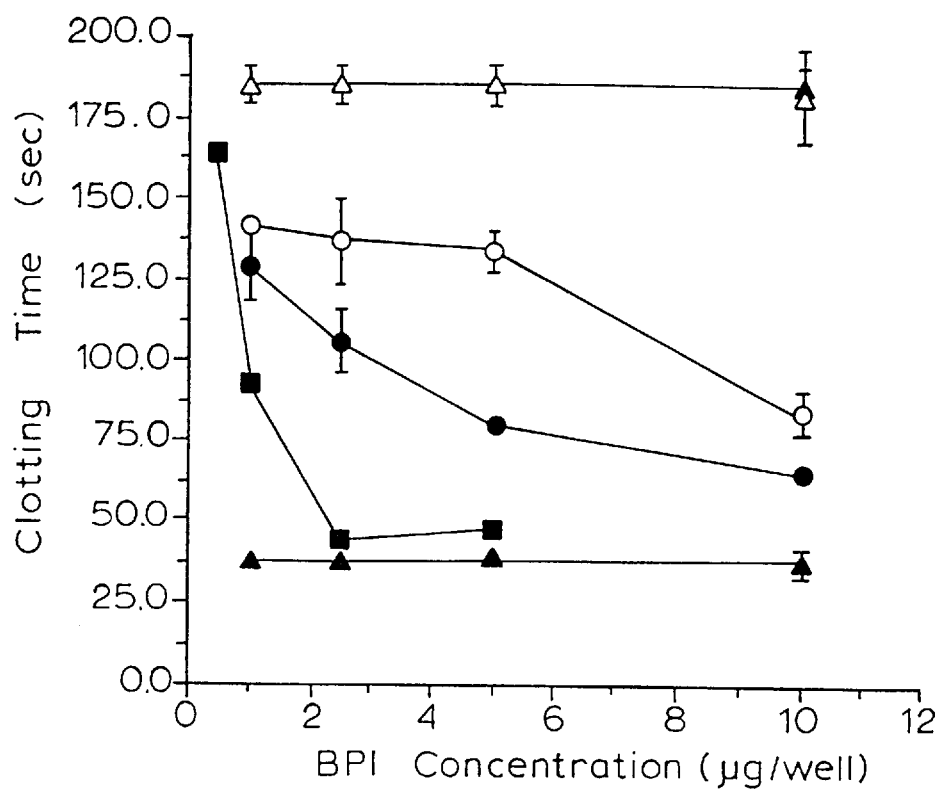
FIG. 12 depicts the effects of BPI protein products on activated partial throinboplastin time (aPTT) time in heparinized plasma.

Heparin Neutralization By BPI Protein Products: Effect Of BPI Dimer On Heparin-Mediated Lengthening Of Activated Partial Thromboplastin Time In Vivo The effect of BPI protein products on heparin-mediated lengthening of activated partial thromboplastin time (aPTT), i.e., the time required for clotting of a mixture of thrombin and plasma was examined. aPTT is lengthened by the presence of exogenous inhibitors of thrombin formation, such as therapeutically administered heparin. Agents which neutralize the anti-coagulant effects of heparin will reduce the aPTT time measured by the test. Human citrated plasma (200 μL) was incubated for 1 minute at 37° C. with either 15 μL of diluent (0.15M NaCl, 0.1M Tris, pH 7.4) or 15 μL of the diluent also containing 25 μg/mL heparin (187 units/mg). Various concentrations of fermenter produced rBPI23, BPI dimer, and rBPI$_2$Δcys in a volume of 15 μL were added, followed immediately by 100 μL of thrombin reagent (Sigma Chemical Co., No. 845-4). aPTT was measured using a BBL Fibrometer (Becton Dickenson Microbiology Systems, Cockeysville, Md.) with the results shown in FIG. 12. The data is depicted as follows: —●—, rBPI$_{23}$; —○—, rBPI$_2$Δcys; —▼—, BPI dimer; —Δ—, PBS buffer; —▲—, no heparin. Specifically, the data establish that both rBPI$_{23}$ and rBPI$_{21}$Δcys inhibit the heparin-mediated lengthening of aPTT but that BPI dimer does so at substantially lower concentrations.

Figure 13:
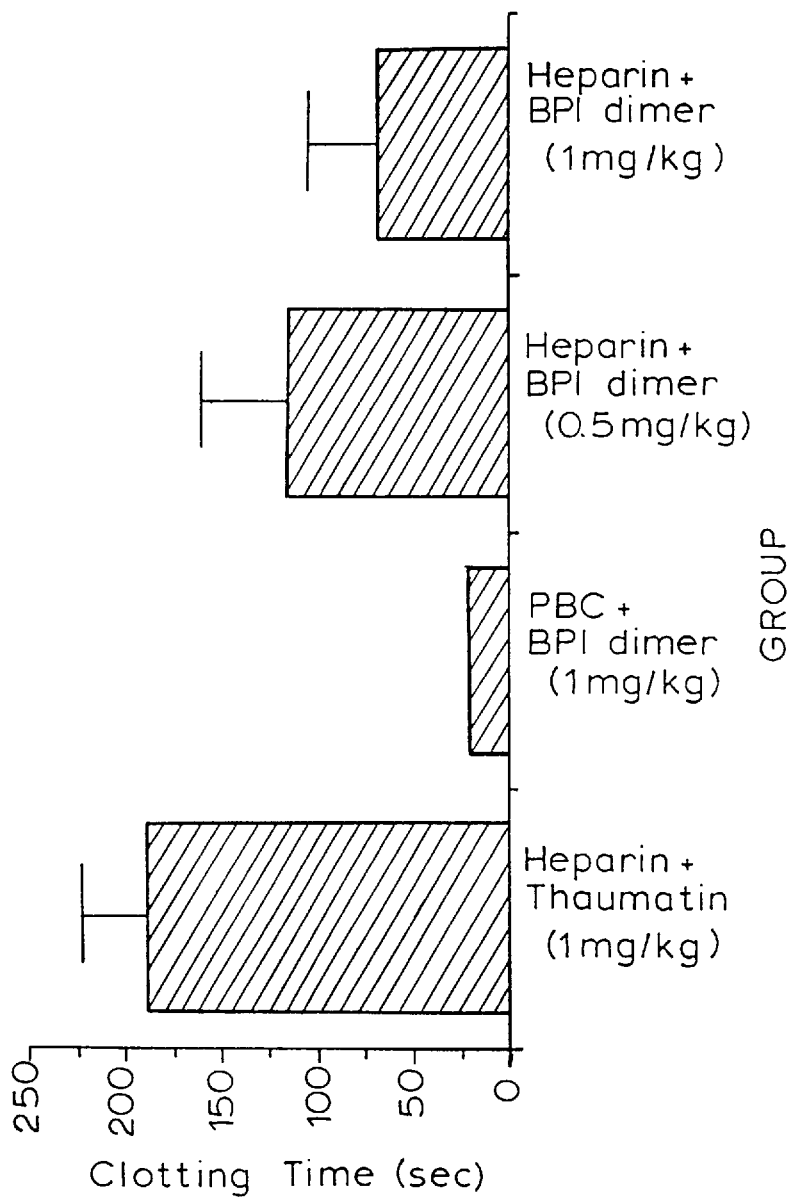
FIG. 13 depicts the effects of BPI protein products on activated partial thromboplastin time (aPTT) in heparin-treated rats.

The effect of BPI dimer on partial thromboplastin time (aPTT) in heparinized rats was determined. aPTT is lengthened by the presence of endogenous or exogenous inhibitors of thrombin formation, such as therapeutically administered heparin. Agents which neutralize the anti-coagulant effects of heparin will reduce the aPTT as measured by the test. Sprague-Dawley rats housed under NIH guidelines and anesthetized by Metaphane® inhalation were administered with 100 U/kg heparin by bolus intravenous injections via the tail vein followed ten minutes later by intravenous administration of 0.5 or 1.0 mg/kg BPI dimer, or 1 mg/kg thaumatin control protein (having charge and size similar to rBPI$_{23}$). Five minutes later, blood samples were collected from the abdominal aorta, plasma was separated therefrom and the aPTT was then determined. The aPTT of a group of non-heparinized PBS treated animals treated with 1 mg/kg rBPI$_{23}$ was also determined. The results shown in FIG. 13 establish that the BPI dimer significantly reduced the aPTT of the treated animals. These animal data confirm, in vivo, the heparin neutralizing effects of BPI dimer as shown above.

EXAMPLE 17

Heparin Neutralization By BPI Protein Products: Effect Of BPI In a Matrigel™ Model of Angiogenesis In this example, the ability of BPI dimer to neutralize heparin in a Matrigel™ model of angiogenesis is determined. The Matrigel™ model described by Passaniti et al., Lab. Invest. 67: 519–528 (1992) uses a basement membrane preparation mixed with FGF 1 or PGF 2 and heparin (40U/mL). The mixture induces an intense vascular response when injected subcutaneously into mice and the extent of angiogenesis is quantitated by measurement of the hemoglobin content of the gels. Compounds which neutralize the angiogenic properties of heparin will inhibit angiogenesis in the Matrigel™ model.

Specifically, Matrigel™ (Collaborative Biomedical Products) is maintained at 4° C. as angiogenic factors are added to the gel in its liquid state. Heparin Sodium (is dissolved in sterile phosphate-buffered saline to various concentrations from 10,000–1,250 U/mL. Recombinant bhFGF (BACHEM Bioscience, Inc.) is diluted with sterile PBS to 200 ng/mL. A volume of 2.5 µL dissolved Heparin Sodium and 2.5 µL recombinant bhFGF is added to 0.5 mL Matrigel™ per mouse injection. BPI dimer is added at 10 µL (1 mg/mL) per 0.5 ml Matrigel™. Sterile PBS is added at 10 µL per injection to those Matrigel™ mixtures not comprising the BPI dimer. Prepared Matrigel™ mixtures are vortexed and drawn into pre-cooled syringes.

Male C57BL/6J mice (Jackson Lab, Bar Harbor, Me.) are 6–8 weeks of age when Matrigel™ mixtures are subcutaneously injected with 0.5 mL of the mixture near the abdominal midline. Seven days subsequent to injections gels are excised and placed in 500 pL Drabkin's reagent. Total protein and hemoglobin content are determined for the gels stored in Drabkin's reagent after homogenization of the gels.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

---

We claim:

1. A bactericidal/permeability-increasing protein (BPI) protein product pharmaceutical composition containing greater than 50 percent of a stable dimeric BPI protein product formed by covalent or NotI-covalent linkage of BPI protein product monomers, other than a dimeric BPI protein product formed by the linkage of immunoglobulin portions of BPI-immunoglobulin fusion protein variants, and a pharmaceutically acceptable diluent, adjuvant or carrier, said dimeric BPI protein product characterized by an enhanced in vivo biological activity in comparison to said BPI protein product monomers.

2. The BPI protein product pharmaceutical composition of claim 1 containing greater than 75 percent of said dimeric BPI protein product.

3. The BPI protein product pharmaceutical composition of claim 1 containing greater than 90 percent of said dimeric BPI protein product.

4. The BPI protein product pharmaceutical composition of claim 1 containing greater than 95 percent of said dimeric BPI protein product.

5. The composition of any one of claims 1, 2, 3 or 4 wherein said BPI protein product monomers are amino-terminal BPI fragments having from about 175 to about 199 of the amino-terminal amino acids of BPI.

6. The composition of any one of claims 1,2,3 or 4 wherein said BPI protein product monomers are BPI holoprotein.

7. An improvement in the method of therapeutic use of a BPI protein product wherein the improvement comprises the step of administering to a subject the BPI protein product pharmaceutical composition of claim 2.

8. An improvement in the method of therapeutic use of a BPI protein product wherein the improvement comprises the step of administering to a subject the BPI protein product pharmaceutical composition of claim 3.

9. An improvement in the method of therapeutic use of a BPI protein product wherein the improvement comprises the step of administering to a subject the BPI protein product pharmaceutical composition of claim 4.

10. An improvement in the method of therapeutic use of a BPI protein product wherein the improvement comprises the step of administering to a subject the BPI protein product pharmaceutical composition of claim 5.

11. An improvement in the method of therapeutic use of a BPI protein product wherein the improvement comprises the step of administering to a subject the BPI protein product pharmaceutical composition of claim 6.

12. An improvement in the method of therapeutic use of a BPI protein product wherein the improvement comprises the step of administering to a subject the BPI protein product pharmaceutical composition of claim 1.

13. The improvement of claim 12 wherein the therapeutic use is the neutralization of endotoxin.

14. The improvement of claim 12 wherein the therapeutic use is selected from the group consisting of the treatment of exposure to gram-negative bacterial endotoxin in circulation, endotoxemia, gram-negative bacterial infections mycobacterial infection, and depressed reticuloendothelial cell system function.

15. The improvement of claim 12 wherein the therapeutic use is the neutralization of heparin.

16. The improvement of claim 12 wherein the therapeutic use is selected from the group consisting of neutralization of the anti-coagulant properties of heparin, inhibition of angiogenesis, inhibition of tumor cell proliferation, inhibition of endothelial cell proliferation, and treatment of chronic inflammatory disease states.

* * * * *

UNITED STATES PATENT AND TRADEMARK OFFICE
CERTIFICATE OF CORRECTION

PATENT NO.   : 5,856,302
DATED        : January 5, 1999
INVENTOR(S)  : Ammons et al.

It is certified that error appears in the above-identified patent and that said Letters Patent is hereby corrected as shown below:

Column 43,
Line 45, "NotI-covalent" should be -- non-covalent --.
Line 63, "about 174 to about 199" should be -- about 1 to 175 to about 1 to 199 --.

Column 45,
Line 4, "gram-negative bacterial infections" should be -- gram-negative bacterial infection, --.

Signed and Sealed this

Eighteenth Day of June, 2002

*Attest:*

*Attesting Officer*

JAMES E. ROGAN
*Director of the United States Patent and Trademark Office*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
        ( A ) NAME/KEY: mat_peptide
        ( B ) LOCATION: 124..1491

( x i ) SEQUENCE DESCRIPTION: SEQ ID NO:1:

```
CAGGCCTTGA GGTTTTGGCA GCTCTGGAGG ATG AGA GAG AAC ATG GCC AGG GGC       54
                                 Met Arg Glu Asn Met Ala Arg Gly
                                 -31 -30                 -25

CCT TGC AAC GCG CCG AGA TGG GTG TCC CTG ATG GTG CTC GTC GCC ATA       102
Pro Cys Asn Ala Pro Arg Trp Val Ser Leu Met Val Leu Val Ala Ile
            -20                 -15                 -10

GGC ACC GCC GTG ACA GCG GCC GTC AAC CCT GGC GTC GTG GTC AGG ATC       150
```

| | | | | | | | | | | | | | | | | |
|---|---|---|---|---|---|---|---|---|---|---|---|---|---|---|---|---|
| | Gly | Thr | Ala<br>-5 | Val | Thr | Ala | Ala | Val<br>1 | Asn | Pro | Gly | Val<br>5 | Val | Arg | Ile | |
| TCC | CAG | AAG | GGC | CTG | GAC | TAC | GCC | AGC | CAG | CAG | GGG | ACG | GCC | GCT | CTG | 198 |
| Ser<br>10 | Gln | Lys | Gly | Leu | Asp<br>15 | Tyr | Ala | Ser | Gln | Gln<br>20 | Gly | Thr | Ala | Ala | Leu<br>25 | |
| CAG | AAG | GAG | CTG | AAG | AGG | ATC | AAG | ATT | CCT | GAC | TAC | TCA | GAC | AGC | TTT | 246 |
| Gln | Lys | Glu | Leu | Lys<br>30 | Arg | Ile | Lys | Ile | Pro<br>35 | Asp | Tyr | Ser | Asp | Ser<br>40 | Phe | |
| AAG | ATC | AAG | CAT | CTT | GGG | AAG | GGG | CAT | TAT | AGC | TTC | TAC | AGC | ATG | GAC | 294 |
| Lys | Ile | Lys | His<br>45 | Leu | Gly | Lys | Gly | His<br>50 | Tyr | Ser | Phe | Tyr | Ser<br>55 | Met | Asp | |
| ATC | CGT | GAA | TTC | CAG | CTT | CCC | AGT | TCC | CAG | ATA | AGC | ATG | GTG | CCC | AAT | 342 |
| Ile | Arg | Glu<br>60 | Phe | Gln | Leu | Pro | Ser<br>65 | Ser | Gln | Ile | Ser | Met<br>70 | Val | Pro | Asn | |
| GTG | GGC | CTT | AAG | TTC | TCC | ATC | AGC | AAC | GCC | AAT | ATC | AAG | ATC | AGC | GGG | 390 |
| Val | Gly<br>75 | Leu | Lys | Phe | Ser | Ile<br>80 | Ser | Asn | Ala | Asn | Ile<br>85 | Lys | Ile | Ser | Gly | |
| AAA | TGG | AAG | GCA | CAA | AAG | AGA | TTC | TTA | AAA | ATG | AGC | GGC | AAT | TTT | GAC | 438 |
| Lys<br>90 | Trp | Lys | Ala | Gln | Lys<br>95 | Arg | Phe | Leu | Lys | Met<br>100 | Ser | Gly | Asn | Phe | Asp<br>105 | |
| CTG | AGC | ATA | GAA | GGC | ATG | TCC | ATT | TCG | GCT | GAT | CTG | AAG | CTG | GGC | AGT | 486 |
| Leu | Ser | Ile | Glu | Gly<br>110 | Met | Ser | Ile | Ser | Ala<br>115 | Asp | Leu | Lys | Leu | Gly<br>120 | Ser | |
| AAC | CCC | ACG | TCA | GGC | AAG | CCC | ACC | ATC | ACC | TGC | TCC | AGC | TGC | AGC | AGC | 534 |
| Asn | Pro | Thr | Ser<br>125 | Gly | Lys | Pro | Thr | Ile<br>130 | Thr | Cys | Ser | Ser | Cys<br>135 | Ser | Ser | |
| CAC | ATC | AAC | AGT | GTC | CAC | GTG | CAC | ATC | TCA | AAG | AGC | AAA | GTC | GGG | TGG | 582 |
| His | Ile | Asn | Ser<br>140 | Val | His | Val | His<br>145 | Ile | Ser | Lys | Ser | Lys<br>150 | Val | Gly | Trp | |
| CTG | ATC | CAA | CTC | TTC | CAC | AAA | AAA | ATT | GAG | TCT | GCG | CTT | CGA | AAC | AAG | 630 |
| Leu | Ile | Gln<br>155 | Leu | Phe | His | Lys | Lys<br>160 | Ile | Glu | Ser | Ala | Leu<br>165 | Arg | Asn | Lys | |
| ATG | AAC | AGC | CAG | GTC | TGC | GAG | AAA | GTG | ACC | AAT | TCT | GTA | TCC | TCC | AAG | 678 |
| Met<br>170 | Asn | Ser | Gln | Val | Cys<br>175 | Glu | Lys | Val | Thr | Asn<br>180 | Ser | Val | Ser | Ser | Lys<br>185 | |
| CTG | CAA | CCT | TAT | TTC | CAG | ACT | CTG | CCA | GTA | ATG | ACC | AAA | ATA | GAT | TCT | 726 |
| Leu | Gln | Pro | Tyr | Phe<br>190 | Gln | Thr | Leu | Pro | Val<br>195 | Met | Thr | Lys | Ile | Asp<br>200 | Ser | |
| GTG | GCT | GGA | ATC | AAC | TAT | GGT | CTG | GTG | GCA | CCT | CCA | GCA | ACC | ACG | GCT | 774 |
| Val | Ala | Gly | Ile<br>205 | Asn | Tyr | Gly | Leu | Val<br>210 | Ala | Pro | Pro | Ala | Thr<br>215 | Thr | Ala | |
| GAG | ACC | CTG | GAT | GTA | CAG | ATG | AAG | GGG | GAG | TTT | TAC | AGT | GAG | AAC | CAC | 822 |
| Glu | Thr | Leu | Asp<br>220 | Val | Gln | Met | Lys | Gly<br>225 | Glu | Phe | Tyr | Ser | Glu<br>230 | Asn | His | |
| CAC | AAT | CCA | CCT | CCC | TTT | GCT | CCA | CCA | GTG | ATG | GAG | TTT | CCC | GCT | GCC | 870 |
| His | Asn | Pro<br>235 | Pro | Pro | Phe | Ala | Pro<br>240 | Pro | Val | Met | Glu<br>245 | Phe | Pro | Ala | Ala | |
| CAT | GAC | CGC | ATG | GTA | TAC | CTG | GGC | CTC | TCA | GAC | TAC | TTC | TTC | AAC | ACA | 918 |
| His | Asp | Arg | Met<br>250 | Val | Tyr | Leu<br>255 | Gly | Leu | Ser | Asp | Tyr<br>260 | Phe | Phe | Asn | Thr<br>265 | |
| GCC | GGG | CTT | GTA | TAC | CAA | GAG | GCT | GGG | GTC | TTG | AAG | ATG | ACC | CTT | AGA | 966 |
| Ala | Gly | Leu | Val | Tyr<br>270 | Gln | Glu | Ala | Gly | Val<br>275 | Leu | Lys | Met | Thr | Leu<br>280 | Arg | |
| GAT | GAC | ATG | ATT | CCA | AAG | GAG | TCC | AAA | TTT | CGA | CTG | ACA | ACC | AAG | TTC | 1014 |
| Asp | Asp | Met | Ile<br>285 | Pro | Lys | Glu | Ser | Lys<br>290 | Phe | Arg | Leu | Thr | Thr<br>295 | Lys | Phe | |
| TTT | GGA | ACC | TTC | CTA | CCT | GAG | GTG | GCC | AAG | AAG | TTT | CCC | AAC | ATG | AAG | 1062 |
| Phe | Gly | Thr<br>300 | Phe | Leu | Pro | Glu | Val<br>305 | Ala | Lys | Lys | Phe | Pro<br>310 | Asn | Met | Lys | |
| ATA | CAG | ATC | CAT | GTC | TCA | GCC | TCC | ACC | CCG | CCA | CAC | CTG | TCT | GTG | CAG | 1110 |

| Ile | Gln | Ile | His | Val | Ser | Ala | Ser | Thr | Pro | Pro | His | Leu | Ser | Val | Gln | |
|-----|-----|-----|-----|-----|-----|-----|-----|-----|-----|-----|-----|-----|-----|-----|-----|-----|
|     | 315 |     |     |     | 320 |     |     |     |     | 325 |     |     |     |     |     |     |

| CCC | ACC | GGC | CTT | ACC | TTC | TAC | CCT | GCC | GTG | GAT | GTC | CAG | GCC | TTT | GCC | 1158 |
|-----|-----|-----|-----|-----|-----|-----|-----|-----|-----|-----|-----|-----|-----|-----|-----|------|
| Pro | Thr | Gly | Leu | Thr | Phe | Tyr | Pro | Ala | Val | Asp | Val | Gln | Ala | Phe | Ala |      |
| 330 |     |     |     |     | 335 |     |     |     |     | 340 |     |     |     |     | 345 |      |

| GTC | CTC | CCC | AAC | TCC | TCC | CTG | GCT | TCC | CTC | TTC | CTG | ATT | GGC | ATG | CAC | 1206 |
|-----|-----|-----|-----|-----|-----|-----|-----|-----|-----|-----|-----|-----|-----|-----|-----|------|
| Val | Leu | Pro | Asn | Ser | Ser | Leu | Ala | Ser | Leu | Phe | Leu | Ile | Gly | Met | His |      |
|     |     |     |     | 350 |     |     |     |     | 355 |     |     |     |     | 360 |     |      |

| ACA | ACT | GGT | TCC | ATG | GAG | GTC | AGC | GCC | GAG | TCC | AAC | AGG | CTT | GTT | GGA | 1254 |
|-----|-----|-----|-----|-----|-----|-----|-----|-----|-----|-----|-----|-----|-----|-----|-----|------|
| Thr | Thr | Gly | Ser | Met | Glu | Val | Ser | Ala | Glu | Ser | Asn | Arg | Leu | Val | Gly |      |
|     |     |     | 365 |     |     |     |     | 370 |     |     |     |     | 375 |     |     |      |

| GAG | CTC | AAG | CTG | GAT | AGG | CTG | CTC | CTG | GAA | CTG | AAG | CAC | TCA | AAT | ATT | 1302 |
|-----|-----|-----|-----|-----|-----|-----|-----|-----|-----|-----|-----|-----|-----|-----|-----|------|
| Glu | Leu | Lys | Leu | Asp | Arg | Leu | Leu | Leu | Glu | Leu | Lys | His | Ser | Asn | Ile |      |
|     |     | 380 |     |     |     |     | 385 |     |     |     |     | 390 |     |     |     |      |

| GGC | CCC | TTC | CCG | GTT | GAA | TTG | CTG | CAG | GAT | ATC | ATG | AAC | TAC | ATT | GTA | 1350 |
|-----|-----|-----|-----|-----|-----|-----|-----|-----|-----|-----|-----|-----|-----|-----|-----|------|
| Gly | Pro | Phe | Pro | Val | Glu | Leu | Leu | Gln | Asp | Ile | Met | Asn | Tyr | Ile | Val |      |
|     | 395 |     |     |     |     | 400 |     |     |     |     | 405 |     |     |     |     |      |

| CCC | ATT | CTT | GTG | CTG | CCC | AGG | GTT | AAC | GAG | AAA | CTA | CAG | AAA | GGC | TTC | 1398 |
|-----|-----|-----|-----|-----|-----|-----|-----|-----|-----|-----|-----|-----|-----|-----|-----|------|
| Pro | Ile | Leu | Val | Leu | Pro | Arg | Val | Asn | Glu | Lys | Leu | Gln | Lys | Gly | Phe |      |
| 410 |     |     |     |     | 415 |     |     |     |     | 420 |     |     |     |     | 425 |      |

| CCT | CTC | CCG | ACG | CCG | GCC | AGA | GTC | CAG | CTC | TAC | AAC | GTA | GTG | CTT | CAG | 1446 |
|-----|-----|-----|-----|-----|-----|-----|-----|-----|-----|-----|-----|-----|-----|-----|-----|------|
| Pro | Leu | Pro | Thr | Pro | Ala | Arg | Val | Gln | Leu | Tyr | Asn | Val | Val | Leu | Gln |      |
|     |     |     |     | 430 |     |     |     |     | 435 |     |     |     |     | 440 |     |      |

| CCT | CAC | CAG | AAC | TTC | CTG | CTG | TTC | GGT | GCA | GAC | GTT | GTC | TAT | AAA |  | 1491 |
|-----|-----|-----|-----|-----|-----|-----|-----|-----|-----|-----|-----|-----|-----|-----|--|------|
| Pro | His | Gln | Asn | Phe | Leu | Leu | Phe | Gly | Ala | Asp | Val | Val | Tyr | Lys |  |      |
|     |     |     | 445 |     |     |     |     | 450 |     |     |     |     | 455 |     |  |      |

| TGAAGGCACC | AGGGGTGCCG | GGGGCTGTCA | GCCGCACCTG | TTCCTGATGG | GCTGTGGGGC | 1551 |
|------------|------------|------------|------------|------------|------------|------|
| ACCGGCTGCC | TTTCCCCAGG | GAATCCTCTC | CAGATCTTAA | CCAAGAGCCC | CTTGCAAACT | 1611 |
| TCTTCGACTC | AGATTCAGAA | ATGATCTAAA | CACGAGGAAA | CATTATTCAT | TGGAAAAGTG | 1671 |
| CATGGTGTGT | ATTTTAGGGA | TTATGAGCTT | CTTTCAAGGG | CTAAGGCTGC | AGAGATATTT | 1731 |
| CCTCCAGGAA | TCGTGTTTCA | ATTGTAACCA | AGAAATTTCC | ATTTGTGCTT | CATGAAAAAA | 1791 |
| AACTTCTGGT | TTTTTTCATG | TG         |            |            |            | 1813 |

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Arg | Glu | Asn | Met | Ala | Arg | Gly | Pro | Cys | Asn | Ala | Pro | Arg | Trp | Val |
|-----|-----|-----|-----|-----|-----|-----|-----|-----|-----|-----|-----|-----|-----|-----|-----|
| -31 | -30 |     |     |     |     | -25 |     |     |     |     | -20 |     |     |     |     |

| Ser | Leu | Met | Val | Leu | Val | Ala | Ile | Gly | Thr | Ala | Val | Thr | Ala | Ala | Val |
|-----|-----|-----|-----|-----|-----|-----|-----|-----|-----|-----|-----|-----|-----|-----|-----|
| -15 |     |     |     |     | -10 |     |     |     |     | -5  |     |     |     |     | 1   |

| Asn | Pro | Gly | Val | Val | Val | Arg | Ile | Ser | Gln | Lys | Gly | Leu | Asp | Tyr | Ala |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |

| Ser | Gln | Gln | Gly | Thr | Ala | Ala | Leu | Gln | Lys | Glu | Leu | Lys | Arg | Ile | Lys |
|-----|-----|-----|-----|-----|-----|-----|-----|-----|-----|-----|-----|-----|-----|-----|-----|
|     |     | 20  |     |     |     |     | 25  |     |     |     |     | 30  |     |     |     |

| Ile | Pro | Asp | Tyr | Ser | Asp | Ser | Phe | Lys | Ile | Lys | His | Leu | Gly | Lys | Gly |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| His | Tyr | Ser | Phe | Tyr | Ser | Met | Asp | Ile | Arg | Glu | Phe | Gln | Leu | Pro | Ser |
|-----|-----|-----|-----|-----|-----|-----|-----|-----|-----|-----|-----|-----|-----|-----|-----|
| 50  |     |     |     |     | 55  |     |     |     |     | 60  |     |     |     |     | 65  |

| Ser | Gln | Ile | Ser | Met | Val | Pro | Asn | Val | Gly | Leu | Lys | Phe | Ser | Ile | Ser |
|-----|-----|-----|-----|-----|-----|-----|-----|-----|-----|-----|-----|-----|-----|-----|-----|
|     |     |     |     | 70  |     |     |     |     | 75  |     |     |     |     | 80  |     |

| | | | | | | | | | | | | | | |
|---|---|---|---|---|---|---|---|---|---|---|---|---|---|---|
| Asn | Ala | Asn | Ile<br>85 | Lys | Ile | Ser | Gly | Lys<br>90 | Trp | Lys | Ala | Gln | Lys<br>95 | Arg | Phe |
| Leu | Lys | Met | Ser<br>100 | Gly | Asn | Phe | Asp<br>105 | Leu | Ser | Ile | Glu | Gly<br>110 | Met | Ser | Ile |
| Ser | Ala | Asp<br>115 | Leu | Lys | Leu | Gly<br>120 | Ser | Asn | Pro | Thr | Ser<br>125 | Gly | Lys | Pro | Thr |
| Ile<br>130 | Thr | Cys | Ser | Ser | Cys<br>135 | Ser | Ser | His | Ile | Asn<br>140 | Ser | Val | His | Val | His<br>145 |
| Ile | Ser | Lys | Ser | Lys<br>150 | Val | Gly | Trp | Leu | Ile<br>155 | Gln | Leu | Phe | His | Lys<br>160 | Lys |
| Ile | Glu | Ser | Ala<br>165 | Leu | Arg | Asn | Lys | Met<br>170 | Asn | Ser | Gln | Val | Cys<br>175 | Glu | Lys |
| Val | Thr | Asn<br>180 | Ser | Val | Ser | Ser | Lys<br>185 | Leu | Gln | Pro | Tyr | Phe<br>190 | Gln | Thr | Leu |
| Pro | Val<br>195 | Met | Thr | Lys | Ile | Asp<br>200 | Ser | Val | Ala | Gly | Ile<br>205 | Asn | Tyr | Gly | Leu |
| Val<br>210 | Ala | Pro | Pro | Ala | Thr<br>215 | Thr | Ala | Glu | Thr | Leu<br>220 | Asp | Val | Gln | Met | Lys<br>225 |
| Gly | Glu | Phe | Tyr | Ser<br>230 | Glu | Asn | His | His | Asn<br>235 | Pro | Pro | Pro | Phe | Ala<br>240 | Pro |
| Pro | Val | Met | Glu<br>245 | Phe | Pro | Ala | Ala | His<br>250 | Asp | Arg | Met | Val | Tyr<br>255 | Leu | Gly |
| Leu | Ser | Asp<br>260 | Tyr | Phe | Phe | Asn | Thr<br>265 | Ala | Gly | Leu | Val | Tyr<br>270 | Gln | Glu | Ala |
| Gly | Val<br>275 | Leu | Lys | Met | Thr | Leu<br>280 | Arg | Asp | Asp | Met | Ile<br>285 | Pro | Lys | Glu | Ser |
| Lys<br>290 | Phe | Arg | Leu | Thr | Thr<br>295 | Lys | Phe | Phe | Gly | Thr<br>300 | Phe | Leu | Pro | Glu | Val<br>305 |
| Ala | Lys | Lys | Phe | Pro<br>310 | Asn | Met | Lys | Ile | Gln<br>315 | Ile | His | Val | Ser | Ala<br>320 | Ser |
| Thr | Pro | Pro | His<br>325 | Leu | Ser | Val | Gln | Pro<br>330 | Thr | Gly | Leu | Thr | Phe<br>335 | Tyr | Pro |
| Ala | Val | Asp<br>340 | Val | Gln | Ala | Phe | Ala<br>345 | Val | Leu | Pro | Asn | Ser<br>350 | Ser | Leu | Ala |
| Ser | Leu<br>355 | Phe | Leu | Ile | Gly | Met<br>360 | His | Thr | Thr | Gly | Ser<br>365 | Met | Glu | Val | Ser |
| Ala<br>370 | Glu | Ser | Asn | Arg | Leu<br>375 | Val | Gly | Glu | Leu | Lys<br>380 | Leu | Asp | Arg | Leu | Leu<br>385 |
| Leu | Glu | Leu | Lys | His<br>390 | Ser | Asn | Ile | Gly | Pro<br>395 | Phe | Pro | Val | Glu | Leu<br>400 | Leu |
| Gln | Asp | Ile | Met<br>405 | Asn | Tyr | Ile | Val | Pro<br>410 | Ile | Leu | Val | Leu | Pro<br>415 | Arg | Val |
| Asn | Glu | Lys<br>420 | Leu | Gln | Lys | Gly | Phe<br>425 | Pro | Leu | Pro | Thr | Pro<br>430 | Ala | Arg | Val |
| Gln | Leu<br>435 | Tyr | Asn | Val | Val | Leu<br>440 | Gln | Pro | His | Gln | Asn<br>445 | Phe | Leu | Leu | Phe |
| Gly<br>450 | Ala | Asp | Val | Val | Tyr<br>455 | Lys | | | | | | | | | |

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

AAGCTTGTCG ACCAGGCCTT GAGGT 25

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CTGGAGGCGG TGATGGTG 18

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CTCCAGCAGC CACATCAAC 19

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GAACTTGGTT GTCAGTCG 18

( 2 ) INFORMATION FOR SEQ ID NO:7:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GCCACCRCCA TGG 13

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
ACTGTCGACG CCACCATGGC CAGGGGC                                                       2 7
```

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
CCGCGGCTCG AGCTATATTT TGGTCAT                                                       2 7
```

( 2 ) INFORMATION FOR SEQ ID NO:10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

```
CTGTAGCTCG AGCCGC                                                                   1 6
```

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
GGCTCGAGCT ACAGAGT                                                                  1 7
```